(12) United States Patent
Nano

(10) Patent No.: US 10,894,954 B2
(45) Date of Patent: Jan. 19, 2021

(54) SUBTILISIN VARIANTS AND USES THEREOF

(71) Applicant: UVic Industry Partnerships Inc., Victoria (CA)

(72) Inventor: Francis Edward Nano, Victoria (CA)

(*) Notice: Subject to any disclaimer, the term of this patent is extended or adjusted under 35 U.S.C. 154(b) by 0 days.

(21) Appl. No.: 16/566,732

(22) Filed: Sep. 10, 2019

(65) Prior Publication Data
US 2020/0071687 A1 Mar. 5, 2020

Related U.S. Application Data

(63) Continuation-in-part of application No. 15/742,145, filed as application No. PCT/IB2016/054055 on Jul. 6, 2016, now abandoned.

(60) Provisional application No. 62/188,969, filed on Jul. 6, 2015.

(51) Int. Cl.
| | | |
|---|---|---|
| *C12N 9/54* | (2006.01) | |
| *C12Q 1/6806* | (2018.01) | |
| *C11D 3/386* | (2006.01) | |

(52) U.S. Cl.
CPC ............... *C12N 9/54* (2013.01); *C11D 3/386* (2013.01); *C12Q 1/6806* (2013.01); *C12Y 304/21062* (2013.01)

(58) Field of Classification Search
CPC ........ C12Y 204/21062; C12N 15/1137; C12N 9/54
See application file for complete search history.

(56) References Cited

U.S. PATENT DOCUMENTS

| | | | |
|---|---|---|---|
| 4,554,101 A | 11/1985 | Hopp | |
| 7,510,859 B2 * | 3/2009 | Wieland | C11D 3/38636 424/401 |
| 8,753,861 B2 | 6/2014 | Cascao-Pereira et al. | |

OTHER PUBLICATIONS

Altschul, S.F. 1991. "Amino acid substitution matrices from an information theoretic perspective." Journal of Molecular Biology, 219: 555-665.
States and Altschul, S.F. 1991. "Improved Sensitivity of Nucleic Acid Database Search Using Application-Specific Scoring Matrices" Methods: A companion to Methods in Enzymology 3(1): 66-77.
Davail, S. et al. "Cold Adaptation of Proteins" J. Biol. Chem., 269:17448-17453, 1994.
Dayhoff, M.O., Schwartz, R.M., Orcutt, B.C. 1978. "A model of evolutionary change in proteins." In "Atlas of Protein Sequence and Structure" 5(3) M.O. Dayhoff (ed.), 345-352, National Biomedical Research Foundation, Washington; States, D.J., Gish, W.

Fuchita N, Arita S, Ikuta J, Miura M, Shimomura K, Motoshima H, Watanabe K. "Gly or Ala substitutions for Pro(210)Thr(2ll)Asn(212) at the fJ8-fJ9 tum of subtilisin Carlsberg increase the catalytic rate and decrease thermostability". Biochim Biophys Acta. Apr. 2012; vol. 1824(4), pp. 620-626. Epub Feb. 2, 2012. PubMed PMID: 22326746.
Steven Henikoff and Jorja G. Henikoff. 1992 "Amino acid substitution matrices from protein blocks." Proc. Natl. Acad. Sci. USA. 89(biochemistry): 10915-10919.
Steven Henikoff and Jorja G. Henikoff. 1993. "Performance Evaluation of Amino Acid Substitution Matrices." Proteins: Structure, Function, and Genetics. 17: 49-61.
M.S. Johnson and J.P. Overington. 1993. "A Structural Basis of Sequence Comparisons: An evaluation of scoring methodologies." Journal of Molecular Biology. 233: 716-738.
Karlin, S. and Altschul, S.F. 1990. "Methods for assessing the statistical significance of molecular sequence features by using general scoring schemes" Proc. Natl. Acad. Sci. USA. 87: 2264-2268.
Miyazaki, K. et al. "Directed Evolution Study of Temperature Adaptation in a Psychrophilic Enzyme," J. Mol. Biol297:1015-1026, 2000.
Moran A.J et al. "Heat-labile proteases in molecular biology applications." FEMS Microbiology Letters 187(1): 59-63, 2001.
Applications of Enzyme Biotechnology. eds Kelly JW, Baldwin TO (Plenum Press, New York, N.Y), pp. 261-272).
Wintrode P.L., et al. "Cold Adaptation of a Mesophilic Subtilisin-like Protease by Laboratory Evolution." J. Biol. Chem. 275: 31635-31640, 2000.
Zhang, X-Z and Zhang Y-H. P. Simple, fast and high-efficiency transformation system for directed evolution of cellulose in Bacillus subtilis, MicrobBiotechnol. 4(1): 98-105, 2011.
Zyprian E, Matzura H., Characterization of signals promoting gene expression on the *Staphylococcus aureus* plasmid pUB110 and development of a gram-positive expression vector system. DNA. Jun. 1986;5(3):219-25; PMID: 3013549.
Ikemura Haruo et al, "In Vitro Processing of Pro-Subtilisin Produced in *Escherichia coli*", The Journal of Biological Chemistry, vol. 263, No. 26, Sep. 15, 1988, pp. 12959-12963.
P. Egnell et al., The autocatalytic processing of the subtilisin Carlsberg pro-region is independent of the primary structure of the cleavage site. Molecular Microbiology (1992) 6(9), 1115-1119.
Jacobs et al., Cloning, sequencing and expression of subtilisin Carlsberg from Bacillus licheniformis. Nucleic Acids Research (1985) 8913-26.
Schulein et al., Preprosubtilisin Carlsberg processing and secretion is blocked after deletion of amino acids 97-101 in the mature part of the enzyme. Mol Gen Genet (1991) 227:137-143.

(Continued)

*Primary Examiner* — Karen Cochrane Carlson
(74) *Attorney, Agent, or Firm* — Klarquist Sparkman, LLP

(57) ABSTRACT

The present invention relates to subtilisin variants and uses thereof. More specifically, the present invention relates to variant subtilisin Carlsberg sequences and uses thereof.

20 Claims, 15 Drawing Sheets
Specification includes a Sequence Listing.

(56) References Cited

OTHER PUBLICATIONS

Smith et al., The Complete Amino Acid Sequence of Two Types of Substilisin, BPN and Carlsberg. The Journal of Biological Chemistry (1966) 5974-76.
Smith et al., The Complete Sequence; Comparison with Substilisin BPN; Evolutionary Relationships. The Journal of Biological Chemistry (1968) 2184-91.

* cited by examiner

```
acagcccaagctttctagagtcCATATAGGATAGGAGATTGATGTATGATGAGGAAAAAGAGTTTTTGGCTT
GGGATGCTGACGGCCTTCATGCTCGTGTTCACGATGGCATTCAGCGATTCCGCTTCTGCTGCTCAACCGGCG
AAAAATGTTGAAAAGGATTATATTGTCGGATTTAAGTCAGGAGTGAAAACCGCATCTGTCAAAAAGGACATC
ATCAAAGAGAGCGGCGGAAAAGTGGACAAGCAGTTTAGAATCATCAACGCGGCAAAAGCGAAGCTAGACAAA
GAAGCGCTTAAGGAAGTCAAAAATGATCCGGATGTCGCTTATGTGGAAGAGGATCATGTGGCCCATGCCTTG
GCGCAAACCGTTCCTTACGGCATTCCTCTCATTAAAGCGGACAAAGTGCAGGCTCAAGGCTTTAAGGGAGCG
AATGTAAAAGTAGCCGTCCTGGATACAGGAATCCAAGCTTCTCATCCGGACTTGAACGTAGTCGGCGGAGCA
AGCTTTGTGGCTGGCGAAGCTTATAACACCGACGGCAACGGACACGGCACACATGTTGCCGGTACAGTAGCT
GCGCTTGACAATACAACGGGTGTATTAGGCGTTGCGCCAAGCGTATCCTTGTACGCGGTTAAAGTACTGAAT
TCAAGCGGAAGCGGATCATACAGCGGCATTGTAAGCGGAATCGAGTGGGCGACAACAAACGGCATGGATGTT
ATCAATATGAGCCTTGGGGGAGCATCAGGCTCGACAGCGATGAAACAGGCAGTCGACAATGCATATGCAAAA
GGGGTTGTCGTTGTAGCTGCAGCAGGGAACAGCGGATCTTCAGGAAACACGAATACAATTGGCTATCCTGCG
AAATACGATTCTGTCATCGCTGTTGGTGCGGTAGACTCTAACAGCAACAGAGCTTCATTTTCCAGTGTGGGA
GCAGAGCTTGAAGTCATGGCTCCTGGCGCAGGCGTATACAGCACTTACCCAACGAACACTTATGCAACATTG
AACGGAACGTCAATGGCTTCTCCTCATGTAGCGGGAGCAGCAGCTTTGATCTTGTCAAAACATCCGAACCTT
TCAGCTTCACAAGTCCGCAACCGTCTCTCCAGCACGGCGACTTATTTGGGAAGCTCCTTCTACTATGGGAAA
GGTCTGATCAATGTCGAAGCTGCCGCTCAACATCACCACCATCACCATTAATGAGATCAACAGTTTGGGCAG
TTgacggatccggggaattc (SEQ ID NO: 1)
```

Figure 1A

MMRKKSFWLGMLTAFMLVFTMAFSDSASAAQPAKNVEKDYIVGFKSGVKTASVKKDIIKESGGKVDKQFRII
NAAKAKLDKEALKEVKNDPDVAYVEEDHVAHALAQTVPYGIPLIKADKVQAQGFKGANVKVAVLDTGIQASH
PDLNVVGGASFVAGEAYNTDGNGHGTHVAGTVAALDNTTGVLGVAPSVSLYAVKVLNSSGSGSYSGIVSGIE
WATTNGMDVINMSLGGASGSTAMKQAVDNAYAKGVVVVAAAGNSGSSGNTNTIGYPAKYDSVIAVGAVDSNS
NRASFSSVGAELEVMAPGAGVYSTYPTNTYATLNGTSMASPHVAGAAALILSKHPNLSASQVRNRLSSTATY
LGSSFYYGKGLINVEAAAQ (SEQ ID NO: 2)

Figure 1B

AQPAKNVEKDYIVGFKSGVKTASVKKDIIKESGGKVDKQFRIINAAKAKLDKEALKEVKNDPDVAYVEEDHV
AHALAQTVPYGIPLIKADKVQAQGFKGANVKVAVLDTGIQASHPDLNVVGGASFVAGEAYNTDGNGHGTHVA
GTVAALDNTTGVLGVAPSVSLYAVKVLNSSGSGSYSGIVSGIEWATTNGMDVINMSLGGASGSTAMKQAVDN
AYAKGVVVVAAAGNSGSSGNTNTIGYPAKYDSVIAVGAVDSNSNRASFSSVGAELEVMAPGAGVYSTYPTNT
YATLNGTSMASPHVAGAAALILSKHPNLSASQVRNRLSSTATYLGSSFYYGKGLINVEAAAQ (SEQ ID
NO: 27)

Figure 1C

AQTVPYGIPLIKADKVQAQGFKGANVKVAVLDTGIQASHPDLNVVGGASFVAGEAYNTDGNGHGTHVAGTVA
ALDNTTGVLGVAPSVSLYAVKVLNSSGSGSYSGIVSGIEWATTNGMDVINMSLGGASGSTAMKQAVDNAYAK
GVVVVAAAGNSGSSGNTNTIGYPAKYDSVIAVGAVDSNSNRASFSSVGAELEVMAPGAGVYSTYPTNTYATL
NGTSMASPHVAGAAALILSKHPNLSASQVRNRLSSTATYLGSSFYYGKGLINVEAAAQ (SEQ ID NO:
28)

Figure 1D

ATGATGAGGAAAAAGAGTTTTTGGCTTGGGATGCTGACGGCCTTCATGCTCGTGTTCACGATGGCATTCAGC
GATTCCGCTTCTGCTGCTCAACCGGCGAAAAATGTTGAAAAGGATTATATTGTCGGATTTAAGTCAGGAGTG
AAAACCGCATCTGTCAAAAAGGACATCATCAAAGAGAGCGGCGGAAAAGTGGACAAGCAGTTTAGAATCATC
AACGCGGCAAAAGCGAAGCTAGACAAAGAAGCGCTTAAGGAAGTCAAAAATGATCCGGATGTCGCTTATGTG
GAAGAGGATCATGTGGCCCATGCCTTGGCGCAAACCGTTCCTTACGGCATTCCTCTCATTAAAGCGGACAAA
GTGCAGGCTCAAGGCTTTAAGGGAGCGAATGTAAAAGTAGCCGTCCTGGATACAGGAATCCAAGCTTCTCAT
CCGGACTTGAACGTAGTCGGCGGAGCAAGCTTTGTGGCTGGCGAGGCTTATAACACCGACGGCAACGGACAC
GGCACACATGTTGCCGGTACAGTAGCTGCGCTTGGCAATACAACGGGTGTATTAGGCGTTGCGCCAAGCGTA
TCCTTGTACGCGGTTAAAGTACTGAATTCAAGCGGAAGCGGATCATACAGCGGCATTGTAAGCGGAATCGAG
TGGGCGACAACAAACGGCATGGATGTTATCAATATGAGCCTTGGGGGAGCATCAGGCTCGACAGCGATGAAA
CAGGCAGTCGACAATGCATATGCAAAAGGGGTTGTCGTTGTAGCTGCAGCAGGGAACAGCGGATCTTCAGGA
AACACGAATACAATTGGCTATCCTGCGAAATACGATTCTGTCATCGCTGTTGGTGCGGTAGACTCTAACAGC
AACAGAGCTTCATTTTCCAGTGTGGGAGCAGAGCTTGAAGTCATGGCTCCTGGCGCAGGCGTATACAGCACT
TACCCAACGAACACTTATGCAACATTGAACGGAACGTCAATGGCTTCTCCTCATGTAGCGGGAGCAGCGGCT
TTGATCATGTCAAAACATCCGAACCTTTCAGCTTCACAAGTCCGCAACCGTCTCTCCAGCACGGCGACTTAT
TGGGAAGCTCCTTCTACTATGGGAAAGGTCTGATCAATGTCGAAGCTGCCGCTC*CA**CATCACCACCATCAC
CAT*TAA(SEQ ID NO: 3)

Figure 2A

ATGATGAGGAAAAAGAGTTTTTGGCTTGGGATGCTGACGGCCTTCATGCTCGTGTTCACGATGGCATTCAGC
GATTCCGCTTCTGCTGCTCAACCGGCGAAAAATGTTGAAAAGGATTATATTGTCGGATTTAAGTCAGGAGTG
AAAACCGCATCTGTCAAAAAGGACATCATCAAAGAGAGCGGCGGAAAAGTGGACAAGCAGTTTAGAATCATC
AACGCGGCAAAAGCGAAGCTAGACAAAGAAGCGCTTAAGGAAGTCAAAAATGATCCGGATGTCGCTTATGTG
GAAGAGGATCATGTGGCCCATGCCTTGGCGCAAACCGTTCCTTACGGCATTCCTCTCATTAAAGCGGACAAA
GTGCAGGCTCAAGGCTTTAAGGGAGCGAATGTAAAAGTAGCCGTCCTGGATACAGGAATCCAAGCTTCTCAT
CCGGACTTGAACGTAGTCGGCGGAGCAAGCTTTGTGGCTGGCGAGGCTTATAACACCGACGGCAACGGACAC
GGCACACATGTTGCCGGTACAGTAGCTGCGCTTGGCAATACAACGGGTGTATTAGGCGTTGCGCCAAGCGTA
TCCTTGTACGCGGTTAAAGTACTGAATTCAAGCGGAAGCGGATCATACAGCGGCATTGTAAGCGGAATCGAG
TGGGCGACAACAAACGGCATGGATGTTATCAATATGAGCCTTGGGGGAGCATCAGGCTCGACAGCGATGAAA
CAGGCAGTCGACAATGCATATGCAAAAGGGGTTGTCGTTGTAGCTGCAGCAGGGAACAGCGGATCTTCAGGA
AACACGAATACAATTGGCTATCCTGCGAAATACGATTCTGTCATCGCTGTTGGTGCGGTAGACTCTAACAGC
AACAGAGCTTCATTTTCCAGTGTGGGAGCAGAGCTTGAAGTCATGGCTCCTGGCGCAGGCGTATACAGCACT
TACCCAACGAACACTTATGCAACATTGAACGGAACGTCAATGGCTTCTCCTCATGTAGCGGGAGCAGCGGCT
TTGATCATGTCAAAACATCCGAACCTTTCAGCTTCACAAGTCCGCAACCGTCTCTCCAGCACGGCGACTTAT
TGGGAAGCTCCTTCTACTATGGGAAAGGTCTGATCAATGTCGAAGCTGCCGCTCCATAA(SEQ ID
NO:4)

Figure 2B

ATGATGAGGAAAAAGAGTTTTTGGCTTGGGATGCTGACGGCCTTCATGCTCGTGTTCACGATGGCATTCAGC
GATTCCGCTTCTGCTGCTCAACCGGCGAAAAATGTTGAAAAGGATTATATTGTCGGATTTAAGTCAGGAGTG
AAAACCGCATCTGTCAAAAAGGACATCATCAAAGAGAGCGGCGGAAAAGTGGACAAGCAGTTTAGAATCATC
AACGCGGCAAAAGCGAAGCTAGACAAAGAAGCGCTTAAGGAAGTCAAAAATGATCCGGATGTCGCTTATGTG
GAAGAGGATCATGTGGCCCATGCCTTGGCGCAAACCGTTCCTTACGGCATTCCTCTCATTAAAGCGGACAAA
GTGCAGGCTCAAGGCTTTAAGGGAGCGAATGTAAAAGTAGCCGTCCTGGATACAGGAATCCAAGCTTCTCAT
CCGGACTTGAACGTAGTCGGCGGAGCAAGCTTTGTGGCTGGCGAGGCTTATAACACCGACGGCAACGGACAC
GGCACACATGTTGCCGGTACAGTAGCTGCGCTTGATAATACAACGGGTGTATTAGGCGTTGCGCCAAGCGTA
TCCTTGTACGCGGTTAAAGTACTGAATTCAAGCGGAAGCGGATCATACAGCGGCATTGTAAGCGGAATCGAG
TGGGCGACAACAAACGGCATGGATGTTATCAATATGAGCCTTGGGGGAGCATCAGGCTCGACAGCGATGAAA
CAGGCAGTCGACAATGCATATGCAAAAGGGGTTGTCGTTGTAGCTGCAGCAGGGAACAGCGGATCTTCAGGA
AACACGAATACAATTGGCTATCCTGCGAAATACGATTCTGTCATCGCTGTTGGTGCGGTAGACTCTAACAGC
AACAGAGCTTCATTTTCCAGTGTGGGAGCAGAGCTTGAAGTCATGGCTCCTGGCGCAGGCGTATACAGCACT
TACCCAACGAACACTTATGCAACATTGAACGGAACGTCAATGGCTTCTCCTCATGTAGCGGGAGCAGCGGCT
TTGATCATGTCAAAACATCCGAACCTTTCAGCTTCACAAGTCCGCAACCGTCTCTCCAGCACGGCGACTTAT
TTGGGAAGCTCCTTCTACTATGGGAAAGGTCTGATCAATGTCGAAGCTGCCGCTCCA*CATCACCACCATCAC
CAT*TAA(SEQ ID NO: 5)

Figure 2C

ATGATGAGGAAAAAGAGTTTTTGGCTTGGGATGCTGACGGCCTTCATGCTCGTGTTCACGATGGCATTCAGC
GATTCCGCTTCTGCTGCTCAACCGGCGAAAAATGTTGAAAAGGATTATATTGTCGGATTTAAGTCAGGAGTG
AAAACCGCATCTGTCAAAAAGGACATCATCAAAGAGAGCGGCGGAAAAGTGGACAAGCAGTTTAGAATCATC
AACGCGGCAAAAGCGAAGCTAGACAAAGAAGCGCTTAAGGAAGTCAAAAATGATCCGGATGTCGCTTATGTG
GAAGAGGATCATGTGGCCCATGCCTTGGCGCAAACCGTTCCTTACGGCATTCCTCTCATTAAAGCGGACAAA
GTGCAGGCTCAAGGCTTTAAGGGAGCGAATGTAAAAGTAGCCGTCCTGGATACAGGAATCCAAGCTTCTCAT
CCGGACTTGAACGTAGTCGGCGGAGCAAGCTTTGTGGCTGGCGAGGCTTATAACACCGACGGCAACGGACAC
GGCACACATGTTGCCGGTACAGTAGCTGCGCTTGATAATACAACGGGTGTATTAGGCGTTGCGCCAAGCGTA
TCCTTGTACGCGGTTAAAGTACTGAATTCAAGCGGAAGCGGATCATACAGCGGCATTGTAAGCGGAATCGAG
TGGGCGACAACAAACGGCATGGATGTTATCAATATGAGCCTTGGGGGAGCATCAGGCTCGACAGCGATGAAA
CAGGCAGTCGACAATGCATATGCAAAAGGGGTTGTCGTTGTAGCTGCAGCAGGGAACAGCGGATCTTCAGGA
AACACGAATACAATTGGCTATCCTGCGAAATACGATTCTGTCATCGCTGTTGGTGCGGTAGACTCTAACAGC
AACAGAGCTTCATTTTCCAGTGTGGGAGCAGAGCTTGAAGTCATGGCTCCTGGCGCAGGCGTATACAGCACT
TACCCAACGAACACTTATGCAACATTGAACGGAACGTCAATGGCTTCTCCTCATGTAGCGGGAGCAGCGGCT
TTGATCATGTCAAAACATCCGAACCTTTCAGCTTCACAAGTCCGCAACCGTCTCTCCAGCACGGCGACTTAT
TTGGGAAGCTCCTTCTACTATGGGAAAGGTCTGATCAATGTCGAAGCTGCCGCTCCATAA(SEQ ID
NO:6)

Figure 2D

```
ATGATGAGGAAAAAGAGTTTTTGGCTTGGGATGCTGACGGCCTTCATGCTCGTGTTCACGATGGCATTCAGC
GATTCCGCTTCTGCTGCTCAACCGGCGAAAAATGTTGAAAAGGATTATATTGTCGGATTTAAGTCAGGAGTG
AAAACCGCATCTGTCAAAAAGGACATCATCAAAGAGAGCGGCGGAAAAGTGGACAAGCAGTTTAGAATCATC
AACGCGGCAAAAGCGAAGCTAGACAAAGAAGCGCTTAAGGAAGTCAAAAATGATCCGGATGTCGCTTATGTG
GAAGAGGATCATGTGGCCCATGCCTTGGCGCAAACCGTTCCTTACGGCATTCCTCTCATTAAAGCGGACAAA
GTGCAGGCTCAAGGCTTTAAGGGAGCGAATGTAAAAGTAGCCGTCCTGGATACAGGAATCCAAGCTTCTCAT
CCGGACTTGAACGTAGTCGGCGGAGCAAGCTTTGTGGCTGGCGAGGCTTATAACACCGACGGCAACGGACAC
GGCACACATGTTGCCGGTACAGTAGCTGCGCTTGCAAATACAACGGGTGTATTAGGCGTTGCGCCAAGCGTA
TCCTTGTACGCGGTTAAAGTACTGAATTCAAGCGGAAGCGGATCATACAGCGGCATTGTAAGCGGAATCGAG
TGGGCGACAACAAACGGCATGGATGTTATCAATATGAGCCTTGGGGGAGCATCAGGCTCGACAGCGATGAAA
CAGGCAGTCGACAATGCATATGCAAAAGGGGTTGTCGTTGTAGCTGCAGCAGGGAACAGCGGATCTTCAGGA
AACACGAATACAATTGGCTATCCTGCGAAATACGATTCTGTCATCGCTGTTGGTGCGGTAGACTCTAACAGC
AACAGAGCTTCATTTTCCAGTGTGGGAGCAGAGCTTGAAGTCATGGCTCCTGGCGCAGGCGTATACAGCACT
TACCCAACGAACACTTATGCAACATTGAACGGAACGTCAATGGCTTCTCCTCATGTAGCGGGAGCAGCGGCT
TTGATCATGTCAAAACATCCGAACCTTTCAGCTTCACAAGTCCGCAACCGTCTCTCCAGCACGGCGACTTAT
TTGGGAAGCTCCTTCTACTATGGGAAAGGTCTGATCAATGTCGAAGCTGCCGCTCA*CATCACCACCATCAC
CAT*TAA (SEQ ID NO: 7)
```

Figure 2E

```
ATGATGAGGAAAAAGAGTTTTTGGCTTGGGATGCTGACGGCCTTCATGCTCGTGTTCACGATGGCATTCAGC
GATTCCGCTTCTGCTGCTCAACCGGCGAAAAATGTTGAAAAGGATTATATTGTCGGATTTAAGTCAGGAGTG
AAAACCGCATCTGTCAAAAAGGACATCATCAAAGAGAGCGGCGGAAAAGTGGACAAGCAGTTTAGAATCATC
AACGCGGCAAAAGCGAAGCTAGACAAAGAAGCGCTTAAGGAAGTCAAAAATGATCCGGATGTCGCTTATGTG
GAAGAGGATCATGTGGCCCATGCCTTGGCGCAAACCGTTCCTTACGGCATTCCTCTCATTAAAGCGGACAAA
GTGCAGGCTCAAGGCTTTAAGGGAGCGAATGTAAAAGTAGCCGTCCTGGATACAGGAATCCAAGCTTCTCAT
CCGGACTTGAACGTAGTCGGCGGAGCAAGCTTTGTGGCTGGCGAGGCTTATAACACCGACGGCAACGGACAC
GGCACACATGTTGCCGGTACAGTAGCTGCGCTTGCAAATACAACGGGTGTATTAGGCGTTGCGCCAAGCGTA
TCCTTGTACGCGGTTAAAGTACTGAATTCAAGCGGAAGCGGATCATACAGCGGCATTGTAAGCGGAATCGAG
TGGGCGACAACAAACGGCATGGATGTTATCAATATGAGCCTTGGGGGAGCATCAGGCTCGACAGCGATGAAA
CAGGCAGTCGACAATGCATATGCAAAAGGGGTTGTCGTTGTAGCTGCAGCAGGGAACAGCGGATCTTCAGGA
AACACGAATACAATTGGCTATCCTGCGAAATACGATTCTGTCATCGCTGTTGGTGCGGTAGACTCTAACAGC
AACAGAGCTTCATTTTCCAGTGTGGGAGCAGAGCTTGAAGTCATGGCTCCTGGCGCAGGCGTATACAGCACT
TACCCAACGAACACTTATGCAACATTGAACGGAACGTCAATGGCTTCTCCTCATGTAGCGGGAGCAGCGGCT
TTGATCATGTCAAAACATCCGAACCTTTCAGCTTCACAAGTCCGCAACCGTCTCTCCAGCACGGCGACTTAT
TTGGGAAGCTCCTTCTACTATGGGAAAGGTCTGATCAATGTCGAAGCTGCCGCTCCATAA(SEQ ID NO:
8)
```

Figure 2F

```
MMRKKSFWLGMLTAFMLVFTMAFSDSASAAQPAKNVEKDYIVGFKSGVKTASVKKDIIKESGGKVDKQFRII
NAAKAKLDKEALKEVKNDPDVAYVEEDHVAHALAQTVPYGIPLIKADKVQAQGFKGANVKVAVLDTGIQASH
PDLNVVGGASFVAGEAYNTDGNGHGTHVAGTVAALGNTTGVLGVAPSVSLYAVKVLNSSGSGSYSGIVSGIE
WATTNGMDVINMSLGGASGSTAMKQAVDNAYAKGVVVVAAAGNSGSSGNTNTIGYPAKYDSVIAVGAVDSNS
NRASFSSVGAELEVMAPGAGVYSTYPTNTYATLNGTSMASPHVAGAAALIMSKHPNLSASQVRNRLSSTATY
LGSSFYYGKGLINVEAAA***P******HHHHHH*** (SEQ ID NO: 9)
```

Figure 2G

```
MMRKKSFWLGMLTAFMLVFTMAFSDSASAAQPAKNVEKDYIVGFKSGVKTASVKKDIIKESGGKVDKQFRII
NAAKAKLDKEALKEVKNDPDVAYVEEDHVAHALAQTVPYGIPLIKADKVQAQGFKGANVKVAVLDTGIQASH
PDLNVVGGASFVAGEAYNTDGNGHGTHVAGTVAALGNTTGVLGVAPSVSLYAVKVLNSSGSGSYSGIVSGIE
WATTNGMDVINMSLGGASGSTAMKQAVDNAYAKGVVVVAAAGNSGSSGNTNTIGYPAKYDSVIAVGAVDSNS
NRASFSSVGAELEVMAPGAGVYSTYPTNTYATLNGTSMASPHVAGAAALIMSKHPNLSASQVRNRLSSTATY
LGSSFYYGKGLINVEAAA***P*** (SEQ ID NO: 10)
```

Figure 2H

```
MMRKKSFWLGMLTAFMLVFTMAFSDSASAAQPAKNVEKDYIVGFKSGVKTASVKKDIIKESGGKVDKQFRII
NAAKAKLDKEALKEVKNDPDVAYVEEDHVAHALAQTVPYGIPLIKADKVQAQGFKGANVKVAVLDTGIQASH
PDLNVVGGASFVAGEAYNTDGNGHGTHVAGTVAALDNTTGVLGVAPSVSLYAVKVLNSSGSGSYSGIVSGIE
WATTNGMDVINMSLGGASGSTAMKQAVDNAYAKGVVVVAAAGNSGSSGNTNTIGYPAKYDSVIAVGAVDSNS
NRASFSSVGAELEVMAPGAGVYSTYPTNTYATLNGTSMASPHVAGAAALIMSKHPNLSASQVRNRLSSTATY
LGSSFYYGKGLINVEAAA***P******HHHHHH*** (SEQ ID NO: 11)
```

Figure 2I

```
MMRKKSFWLGMLTAFMLVFTMAFSDSASAAQPAKNVEKDYIVGFKSGVKTASVKKDIIKESGGKVDKQFRII
NAAKAKLDKEALKEVKNDPDVAYVEEDHVAHALAQTVPYGIPLIKADKVQAQGFKGANVKVAVLDTGIQASH
PDLNVVGGASFVAGEAYNTDGNGHGTHVAGTVAALDNTTGVLGVAPSVSLYAVKVLNSSGSGSYSGIVSGIE
WATTNGMDVINMSLGGASGSTAMKQAVDNAYAKGVVVVAAAGNSGSSGNTNTIGYPAKYDSVIAVGAVDSNS
NRASFSSVGAELEVMAPGAGVYSTYPTNTYATLNGTSMASPHVAGAAALIMSKHPNLSASQVRNRLSSTATY
LGSSFYYGKGLINVEAAA***P*** (SEQ ID NO: 12)
```

Figure 2J

```
MMRKKSFWLGMLTAFMLVFTMAFSDSASAAQPAKNVEKDYIVGFKSGVKTASVKKDIIKESGGKVDKQFRII
NAAKAKLDKEALKEVKNDPDVAYVEEDHVAHALAQTVPYGIPLIKADKVQAQGFKGANVKVAVLDTGIQASH
PDLNVVGGASFVAGEAYNTDGNGHGTHVAGTVAALANTTGVLGVAPSVSLYAVKVLNSSGSGSYSGIVSGIE
WATTNGMDVINMSLGGASGSTAMKQAVDNAYAKGVVVVAAAGNSGSSGNTNTIGYPAKYDSVIAVGAVDSNS
NRASFSSVGAELEVMAPGAGVYSTYPTNTYATLNGTSMASPHVAGAAALIMSKHPNLSASQVRNRLSSTATY
LGSSFYYGKGLINVEAAA***P******HHHHHH*** (SEQ ID NO: 13)
```

Figure 2K

```
MMRKKSFWLGMLTAFMLVFTMAFSDSASAAQPAKNVEKDYIVGFKSGVKTASVKKDIIKESGGKVDKQFRII
NAAKAKLDKEALKEVKNDPDVAYVEEDHVAHALAQTVPYGIPLIKADKVQAQGFKGANVKVAVLDTGIQASH
PDLNVVGGASFVAGEAYNTDGNGHGTHVAGTVAALANTTGVLGVAPSVSLYAVKVLNSSGSGSYSGIVSGIE
WATTNGMDVINMSLGGASGSTAMKQAVDNAYAKGVVVVAAAGNSGSSGNTNTIGYPAKYDSVIAVGAVDSNS
NRASFSSVGAELEVMAPGAGVYSTYPTNTYATLNGTSMASPHVAGAAALIMSKHPNLSASQVRNRLSSTATY
LGSSFYYGKGLINVEAAA***P*** (SEQ ID NO: 14)
```

Figure 2L

AQPAKNVEKDYIVGFKSGVKTASVKKDIIKESGGKVDKQFRIINAAKAKLDKEALKEVKNDPDVAYVEEDHV
AHALAQTVPYGIPLIKADKVQAQGFKGANVKVAVLDTGIQASHPDLNVVGGASFVAGEAYNTDGNGHGTHVA
GTVAALGNTTGVLGVAPSVSLYAVKVLNSSGSGSYSGIVSGIEWATTNGMDVINMSLGGASGSTAMKQAVDN
AYAKGVVVVAAAGNSGSSGNTNTIGYPAKYDSVIAVGAVDSNSNRASFSSVGAELEVMAPGAGVYSTYPTNT
YATLNGTSMASPHVAGAAALIMSKHPNLSASQVRNRLSSTATYLGSSFYYGKGLINVEAAA*PHHHHHH*
(SEQ ID NO: 23)

Figure 2M

AQPAKNVEKDYIVGFKSGVKTASVKKDIIKESGGKVDKQFRIINAAKAKLDKEALKEVKNDPDVAYVEEDHV
AHALAQTVPYGIPLIKADKVQAQGFKGANVKVAVLDTGIQASHPDLNVVGGASFVAGEAYNTDGNGHGTHVA
GTVAALGNTTGVLGVAPSVSLYAVKVLNSSGSGSYSGIVSGIEWATTNGMDVINMSLGGASGSTAMKQAVDN
AYAKGVVVVAAAGNSGSSGNTNTIGYPAKYDSVIAVGAVDSNSNRASFSSVGAELEVMAPGAGVYSTYPTNT
YATLNGTSMASPHVAGAAALIMSKHPNLSASQVRNRLSSTATYLGSSFYYGKGLINVEAAAP (SEQ ID
NO: 24)

Figure 2N

AQTVPYGIPLIKADKVQAQGFKNVKVAVLDTGIQASHPDLNVVGGASFVAGEAYNTDGNGHGTHVAGTVAAL
GNTTGVLGVAPSVSLYAVKVLNSSGSGSYSGIVSGIEWATTNGMDVINMSLGGASGSTAMKQAVDNAYAKGV
VVVAAGNSGSSGNTNTIGYPAKYDSVIAVGAVDSNSNRASFSSVGAELEVMAPGAGYSTYPTNTYATLNGTS
MASPHVAGAAALIMSKHPNLSASQVRNRLSSTATYLGSSFYYGKGLINVEAAA*PHHHHH* (SEQ ID NO:
25)

Figure 2O

AQTVPYGIPLIKADKVQAQGFKNVKVAVLDTGIQASHPDLNVVGGASFVAGEAYNTDGNGHGTHVAGTVAAL
GNTTGVLGVAPSVSLYAVKVLNSSGSGSYSGIVSGIEWATTNGMDVINMSLGGASGSTAMKQAVDNAYAKGV
VVVAAGNSGSSGNTNTIGYPAKYDSVIAVGAVDSNSNRASFSSVGAELEVMAPGAGYSTYPTNTYATLNGTS
MASPHVAGAAALIMSKHPNLSASQVRNRLSSTATYLGSSFYYGKGLINVEAAAP (SEQ ID NO: 26)

Figure 2P

ATGATGAGGAAAAAGAGTTTTTGGCTTGGG
ATGCTGACGGCCTTCATGCTCGTGTTCACGATGGCATTCAGCGATTCCGCTTCTGCTGCTCAACCGGCGAAA
AATGTTGAAAAGGATTATATTGTCGGATTTAAGTCAGGAGTGAAAACCGCATCTGTCAAAAAGGACATCATC
AAAGAGAGCGGCGGAAAAGTGGACAAGCAGTTTAGAATCATCAACGCGGCAAAAGCGAAGCTAGACAAAGAA
GCGCTTAAGGAAGTCAACAATGATCCAGATGTCGCTTATGTGGAAGAGGATCATGTGGCCCATGCCTTGGCG
CAAACCGTTCCTTACGGCATTCCTCTCATTAAAGCGGACAAAGTGCAGGCCCAAGGCTTTAAGGGAGCGAAT
GTAAAAGTAGCCGTCCTGGATACAGGAATCCAAGCTTCTCATCCGGACTTGAACGTAGTCGGCGGAGCAAGC
TTTGTGGCTGGCGAAGCTTATAACACCGACGGCAACGGACACGGCACACATGTTGCCGGTACAGTAGCTGCG
CTTGGCTATACAACGGGTGTATTAGGCGTTGCGCCAAGCGTATCCTTGTACGCGGTTAAAGTACTGAATTCA
AGCGGGAGCGGATCATACAGCGGCATTGTAAGCGGAATCGAGTGGGCGACAACAAACGGCATGGATGTTATC
AATATGAGCCTTGGGGGAGCATCAGGCTCGACAGCGATGAAACAGGCAGTCGACAATGCATATGCAAAGGG
GTTGTCGTTGTAGCTGCAGCAGGGAACAGCGGATCTTCAGGAAGCACGAATACAATTGGCTATCCTGCGAAA
TACGATTCTGTCATCGCTGTTGGTGCGGTAGACTCTAACAGCAACAGAGCTTCATTTTCCAGTGTGGGAGCA
GAGCTTGAAGTCATGGCCCCTGGCGCAGGCGTATACAGCACTTACCCAACGAACACTTATGCAACATTTAAC
GGAACGTCAATGGCTTCTCCTCATGTAGCGGGAGCAGCAGCTTTGATCTTGTCAAAACATCCGAACCTTTCA
GCTTCACAAGTCCGCAACCGTCTCTCCAGCACGGCGACTTATTTGGGAAGCTCCTTCTACTATGGGAAAGGT
CTGATCAATGTCGAAGCTGCCGCTCAA*CATCACCACCATCACCAT*TAA (SEQ ID NO: 15)

Figure 3A

ATGATGAGGAAAAAGAGTTTTTGGCTTGGG
ATGCTGACGGCCTTCATGCTCGTGTTCACGATGGCATTCAGCGATTCCGCTTCTGCTGCTCAACCGGCGAAA
AATGTTGAAAAGGATTATATTGTCGGATTTAAGTCAGGAGTGAAAACCGCATCTGTCAAAAAGGACATCATC
AAAGAGAGCGGCGGAAAAGTGGACAAGCAGTTTAGAATCATCAACGCGGCAAAAGCGAAGCTAGACAAAGAA
GCGCTTAAGGAAGTCAACAATGATCCAGATGTCGCTTATGTGGAAGAGGATCATGTGGCCCATGCCTTGGCG
CAAACCGTTCCTTACGGCATTCCTCTCATTAAAGCGGACAAAGTGCAGGCCCAAGGCTTTAAGGGAGCGAAT
GTAAAAGTAGCCGTCCTGGATACAGGAATCCAAGCTTCTCATCCGGACTTGAACGTAGTCGGCGGAGCAAGC
TTTGTGGCTGGCGAAGCTTATAACACCGACGGCAACGGACACGGCACACATGTTGCCGGTACAGTAGCTGCG
CTTGGCTATACAACGGGTGTATTAGGCGTTGCGCCAAGCGTATCCTTGTACGCGGTTAAAGTACTGAATTCA
AGCGGGAGCGGATCATACAGCGGCATTGTAAGCGGAATCGAGTGGGCGACAACAAACGGCATGGATGTTATC
AATATGAGCCTTGGGGGAGCATCAGGCTCGACAGCGATGAAACAGGCAGTCGACAATGCATATGCAAAGGG
GTTGTCGTTGTAGCTGCAGCAGGGAACAGCGGATCTTCAGGAAGCACGAATACAATTGGCTATCCTGCGAAA
TACGATTCTGTCATCGCTGTTGGTGCGGTAGACTCTAACAGCAACAGAGCTTCATTTTCCAGTGTGGGAGCA
GAGCTTGAAGTCATGGCCCCTGGCGCAGGCGTATACAGCACTTACCCAACGAACACTTATGCAACATTTAAC
GGAACGTCAATGGCTTCTCCTCATGTAGCGGGAGCAGCAGCTTTGATCTTGTCAAAACATCCGAACCTTTCA
GCTTCACAAGTCCGCAACCGTCTCTCCAGCACGGCGACTTATTTGGGAAGCTCCTTCTACTATGGGAAAGGT
CTGATCAATGTCGAAGCTGCCGCTCAATAA (SEQ ID NO: 16)

Figure 3B

MMRKKSFWLGMLTAFMLVFTMAFSDSASAAQPAKNVEKDYIVGFKSGVKTASVKKDIIKESGGKVDKQFRII
NAAKAKLDKEALKEVNNDPDVAYVEEDHVAHALAQTVPYGIPLIKADKVQAQGFKGANVKVAVLDTGIQASH
PDLNVVGGASFVAGEAYNTDGNGHGTHVAGTVAALGYTTGVLGVAPSVSLYAVKVLNSSGSGSYSGIVSGIE
WATTNGMDVINMSLGGASGSTAMKQAVDNAYAKGVVVAAAGNSGSSGSTNTIGYPAKYDSVIAVGAVDSNS
NRASFSSVGAELEVMAPGAGVYSTYPTNTYATFNGTSMASPHVAGAAALILSKHPNLSASQVRNRLSSTATY
LGSSFYYGKGLINVEAAAQ*HHHHHH* (SEQ ID NO: 17)

Figure 3C

MMRKKSFWLGMLTAFMLVFTMAFSDSASAAQPAKNVEKDYIVGFKSGVKTASVKKDIIKESGGKVDKQFRII
NAAKAKLDKEALKEVNNDPDVAYVEEDHVAHALAQTVPYGIPLIKADKVQAQGFKGANVKVAVLDTGIQASH
PDLNVVGGASFVAGEAYNTDGNGHGTHVAGTVAALGYTTGVLGVAPSVSLYAVKVLNSSGSGSYSGIVSGIE
WATTNGMDVINMSLGGASGSTAMKQAVDNAYAKGVVVAAAGNSGSSGSTNTIGYPAKYDSVIAVGAVDSNS
NRASFSSVGAELEVMAPGAGVYSTYPTNTYATFNGTSMASPHVAGAAALILSKHPNLSASQVRNRLSSTATY
LGSSFYYGKGLINVEAAAQ (SEQ ID NO: 18)

Figure 3D

SUBTILISIN VARIANTS AND USES THEREOF

CROSS REFERENCE TO RELATED APPLICATIONS

This is a continuation-in-part of U.S. application Ser. No. 15/742,145, filed Jan. 5, 2018, which is the § 371 U.S. National Stage of International Application No. PCT/IB2016/054055, filed Jul. 6, 2016, which was published in English under PCT Article 21(2), which in turn claims the benefit of U.S. Provisional Application No. 62/188,969, filed Jul. 6, 2015, each of which are incorporated by reference herein in its entirety.

FIELD OF INVENTION

The present invention relates to subtilisin variants and uses thereof. More specifically, the present invention relates to variant subtilisin Carlsberg sequences and uses thereof.

BACKGROUND OF THE INVENTION

Enzymes that denature with moderate heat have an established role in molecular biology. Their time and cost-saving advantage comes from eliminating the need to do a purification step after the role of the enzyme is done. One simply uses a heat-inactivation step; the enzyme denatures, and further manipulations of the bio-molecules or cell-extract can occur. One example is the use of heat-labile restriction enzymes to digest DNA prior to ligation. Useful restriction enzymes include variants that digest DNA at 37° C., and can be heat denatured afterwards, typically by a twenty-minute heating step at 65° C. The alternatives to heat denaturation generally take longer, cost more and result in loss of DNA.

Commonly used proteases include proteinase K and subtilisin. Subtilisin Carlsberg is a serine protease expressed and secreted by *Bacillus licheniformis*. *Bacillus*-encoded subtilisins generally have a signal peptide of about 30 amino acids which precedes a pro-region of about 77 amino acids. The pro-region is removed by autocleavage to generate a mature, active enzyme (Egnell P, Flock J I. The autocatalytic processing of the subtilisin Carlsberg pro-region is independent of the primary structure of the cleavage site. Mol Microbiol. 1992 May; 6(9):1115-9; Schülein R, Kreft J, Gonski S, Goebel W. Preprosubtilisin Carlsberg processing and secretion is blocked after deletion of amino acids 97-101 in the mature part of the enzyme. Mol Gen Genet. 1991 May; 227(1):137-43). In the case of subtilisin Carlsberg, the signal peptide is 29 amino acids long (Jacobs M, Eliasson M, Uhlén M, Flock J I. Cloning, sequencing and expression of subtilisin Carlsberg from *Bacillus licheniformis*. Nucleic Acids Res. 1985 Dec. 20; 13(24):8913-26), the pro-region is 76 amino acids long (Smith E L, DeLange R J, Evans W H, Landon M, Markland F S. Subtilisin Carlsberg. V. The complete sequence; comparison with subtilisin BPN'; evolutionary relationships. J Biol Chem. 1968 May 10; 243(9): 2184-91. PMID: 4967581) and the mature enzyme is 274 amino acids (Smith E L, Markland F S, Kasper C B, DeLange R J, Landon M, Evans W H. The complete amino acid sequence of two types of subtilisin, BPN' and Carlsberg. J Biol Chem. 1966 Dec. 25; 241(24):5974-6. PMID: 4959323; Smith et al., 1968, supra). The mature enzyme may have a molecular weight of about 27,260 Da.

Subtilisin-like proteases have been developed to be active in hot water for stain removers in laundry (U.S. Pat. No. 8,753,861 B2 entitled "Protease comprising one or more combinable mutations"; Kristjansson M M. 2012. Thermostable subtilases (subtilisin-like serine proteinases), p 67-105. In Sen S, Nilsson L (ed), Thermostable proteins: structural stability and design, 1st ed. CRC Press, Boca Raton, Fla.).

A naturally occurring heat-labile metalloprotease (a class of protease different from subtilisin proteases) from a cold ocean water bacterium called A9 was described by Moran et al. (Moran A. J et al. "Heat-labile proteases in molecular biology applications." FEMS Microbiology Letters 187(1): 59-63, 2001). This enzyme is both cold-adapted (has good catalytic activity at cold temperature) and heat-labile (denatures at relatively low temperature) but does not have stability at working temperatures and is prone to autolysis, making its use limited. Directed evolution was used to mutate a similar psychrophilic enzyme, S41 (Davail, S. et al. "Cold Adaptation of Proteins" J. Biol. Chem., 269:17448-17453, 1994) to improve its thermostability and activity while retaining its activity at cool temperatures (Miyazaki, K. et al. "Directed Evolution Study of Temperature Adaptation in a Psychrophilic Enzyme," *J. Mol. Biol* 297:1015-1026, 2000) and a mesophilic enzyme, subtilisin SSII, was also mutated to have low-temperature activity (Wintrode P. L., et al. "Cold Adaptation of a Mesophilic Subtilisin-like Protease by Laboratory Evolution." J. Biol. Chem. 275: 31635-31640, 2000), in studies exploring the evolutionary process of cold or heat adaptation.

SUMMARY OF THE INVENTION

The present invention relates to variant subtilisin Carlsberg sequences and uses thereof.

In some aspects, the invention provides a variant, heat labile subtilisin Carlsberg polypeptide that includes a mutation at one or more of amino acid positions K88, D180, N181, N265, L321, L339 or Q379 as referenced in SEQ ID NO: 2, or combinations thereof, except for the combination of amino acids D180, N265, and L321.

In some embodiments, the variant subtilisin Carlsberg polypeptide includes a mutation at amino acids D180, L339 and Q379; L339 and Q379; D180 and L339; D180 and Q379; or K88, D180, N181, N265, and L321.

In some embodiments, the mutation at K88 is K88N, the mutation at D180 is D180G or D180A, the mutation at N181 is N181Y, the mutation at N265 is N265S, the mutation at L321 is L321F, the mutation at L339 is L339M, or the mutation at Q379 is Q379P.

In some embodiments, the variant subtilisin Carlsberg polypeptide includes the sequence set forth in any one of SEQ ID NOs: 9 to 14, 17, 18, 23, 24, 25 or 26.

In some embodiments, the variant subtilisin Carlsberg polypeptide includes the sequence set forth in SEQ ID NO: 27 or 28, where the polypeptide includes a mutation at amino acid positions: D180; L339; Q379; D180 and L339; D180 and Q379; L339 and Q379; or D180, L339 and Q379 as referenced in SEQ ID NO: 2.

In some aspects, the invention provides a nucleic acid molecule encoding a variant subtilisin Carlsberg polypeptide as described herein.

In some aspects, the invention provides a nucleic acid molecule including the sequence set forth in any one of SEQ ID NOs: 3 to 8, 15 or 16.

In some aspects, the invention provides an expression vector including a nucleic acid molecule as described herein.

In some aspects, the invention provides a host cell including an expression vector as described herein. The host cell may be a *B. subtilis*.

In some aspects, the invention provides a method of removing a target polypeptide from a sample by providing a sample including the target polypeptide and adding a variant subtilisin Carlsberg polypeptide as described herein to the sample for a sufficient period of time and at a suitable temperature to remove the target polypeptide. The method may further include increasing the temperature of the sample (for example, to about 50° C.) to inactivate the variant subtilisin Carlsberg polypeptide as described herein.

The target polypeptide may be a polypeptide used in molecular biology techniques, such as an enzyme (e.g., a heat resistant enzyme, a nuclease, a DNA modifying enzyme, a restriction enzyme), or a contaminant.

The sample may be a preparation of plasmid DNA, a preparation of chromosomal DNA, a preparation of mitochondrial DNA, a preparation of RNA, a forensic sample, a clinical sample, or a diagnostic sample.

In some aspects, the invention provides a composition comprising a polypeptide as described herein and a carrier. In some embodiments, the composition may be a detergent composition.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1A shows the synthetic DNA encoding full length subtilisin Carlsberg used as a target for error prone PCR, with the start (ATG) and stop (TAA) codons underlined; spacer sequences shown in italics; the region encoding the added histidine tag shown in bold italics; codons corresponding to positions 88, 180, 181, 265, 321, 339 and 379 indicated in bold underline, and plasmid vector pZY167 sequences in lower case type (SEQ ID NO: 1);

FIG. 1B shows the polypeptide sequence of full length subtilisin Carlsberg, with the signal peptide shown in bold (amino acids 1-29), the pro-region shown in italics (amino acids 30-105) and the amino acid positions corresponding to amino acids 88, 180, 181, 265, 321, 339 and 379 indicated in bold underline (SEQ ID NO: 2);

FIG. 1C shows the polypeptide sequence of subtilisin Carlsberg proprotein, with the pro-region shown in italics (amino acids 30-105 of SEQ ID NO: 2) and the amino acid positions corresponding to amino acids 88, 180, 181, 265, 321, 339 and 379 of SEQ ID NO: 2 indicated in bold underline (SEQ ID NO: 27);

FIG. 1D shows the polypeptide sequence of subtilisin Carlsberg mature protein, with the amino acid positions corresponding to amino acids 180, 181, 265, 321, 339 and 379 of SEQ ID NO: 2 indicated in bold underline (SEQ ID NO: 28);

FIG. 2A shows the DNA sequence encoding full length subtilisin variant B24, with the start (ATG) and stop (TAA) codons underlined, the nucleotide changes indicated in bold, the associated codons underlined, and the region encoding the added histidine tag shown in bold italics (SEQ ID NO: 3);

FIG. 2B shows the DNA sequence encoding full length subtilisin variant B24, with the start (ATG) and stop (TAA) codons underlined, the nucleotide changes indicated in bold, and the associated codons underlined (SEQ ID NO: 4);

FIG. 2C shows the DNA sequence encoding full length subtilisin variant B24, with a G180D change and with the start (ATG) and stop (TAA) codons underlined, the nucleotide changes indicated in bold, the associated codons underlined, and the region encoding the added histidine tag shown in bold italics (SEQ ID NO: 5);

FIG. 2D shows the DNA sequence encoding full length subtilisin variant B24, with a G180D change and with the start (ATG) and stop (TAA) codons underlined, the nucleotide changes indicated in bold, and the associated codons underlined (SEQ ID NO: 6);

FIG. 2E shows the DNA sequence encoding full length subtilisin variant B24, with a G180A change and with the start (ATG) and stop (TAA) codons underlined, the nucleotide changes indicated in bold, the associated codons underlined, and the region encoding the added histidine tag shown in bold italics (SEQ ID NO: 7);

FIG. 2F shows the DNA sequence encoding full length subtilisin variant B24, with a G180A change and with the start (ATG) and stop (TAA) codons underlined, the nucleotide changes indicated in bold, and the associated codons underlined (SEQ ID NO: 8);

FIG. 2G shows the polypeptide sequence of full length subtilisin variant B24, with the amino acid changes indicated in bold and the added histidine tag shown in bold italics (SEQ ID NO: 9);

FIG. 2H shows the polypeptide sequence of full length subtilisin variant B24, with the amino acid changes indicated in bold (SEQ ID NO: 10);

FIG. 2I shows the polypeptide sequence of full length subtilisin variant B24, with a G180D change and with the amino acid changes indicated in bold and the added histidine tag shown in bold italics (SEQ ID NO: 11);

FIG. 2J shows the polypeptide sequence of full length subtilisin variant B24, with a G180D change and with the amino acid changes indicated in bold (SEQ ID NO: 12);

FIG. 2K shows the polypeptide sequence of full length subtilisin variant B24, with a G180A change and with the amino acid changes indicated in bold and the added histidine tag shown in bold italics (SEQ ID NO: 13);

FIG. 2L shows the polypeptide sequence of full length subtilisin variant B24, with a G180A change and with the amino acid changes indicated in bold (SEQ ID NO: 14);

FIG. 2M shows the polypeptide sequence of subtilisin variant B24 proprotein with the amino acid changes indicated in bold and the added histidine tag shown in bold italics (SEQ ID NO: 23);

FIG. 2N shows the polypeptide sequence of subtilisin variant B24 proprotein with the amino acid changes indicated in bold (SEQ ID NO: 24);

FIG. 2O shows the polypeptide sequence of subtilisin variant B24 mature protein with the amino acid changes indicated in bold and the added histidine tag shown in bold italics (SEQ ID NO: 25);

FIG. 2P shows the polypeptide sequence of subtilisin variant B24 mature protein with the amino acid changes indicated in bold (SEQ ID NO: 26);

FIG. 3A shows the DNA sequence encoding full length subtilisin variant P23, with the start (ATG) and stop (TAA) codons underlined, the nucleotide changes indicated in bold, the associated codons underlined, and the region encoding the added histidine tag shown in bold italics (SEQ ID NO: 15);

FIG. 3B shows the DNA sequence encoding full length subtilisin variant P23, with the start (ATG) and stop (TAA) codons underlined, the nucleotide changes indicated in bold, and the associated codons underlined (SEQ ID NO: 16);

FIG. 3C shows the polypeptide sequence of full length subtilisin variant P23, with the amino acid changes indicated in bold and the added histidine tag shown in bold italics (SEQ ID NO: 17);

FIG. 3D shows the polypeptide sequence of full length subtilisin variant P23, with the amino acid changes indicated in bold (SEQ ID NO: 18);

Figure 4A:
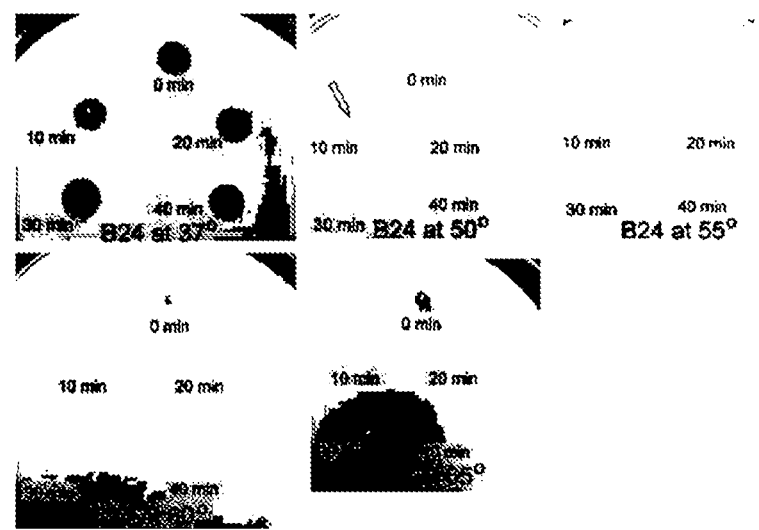
FIG. 4A is a photograph of heat inactivation of Subtilisin Carlsberg variant B24, with loss of activity at 50° C., 55° C., 60° C. and 65° C. within 10 minutes. Activity of protease was detected by spotting 7 µL of culture supernatant of SCK6 (pZY167::B24) that expresses the B24 protease.

The Sequence Listing is submitted as an ASCII text file in the form of the file named Sequence_Listing.txt, which was created on Sep. 10, 2019, and is 63,201 bytes, which is incorporated by reference herein.

DETAILED DESCRIPTION

The present disclosure provides, in part, variant subtilisin Carlsberg molecules and uses thereof. By "variant subtilisin Carlsberg molecules," "subtilisin variant," "variant polypeptides," "variant," or "variants," as used herein, is meant the variant polypeptides including one or more of the mutations described herein, as well as nucleic acid molecules encoding such polypeptides. In some embodiments, the variant subtilisin Carlsberg polypeptides described herein are heat labile. In some embodiments, the variant subtilisin Carlsberg polypeptides described herein are not found in nature i.e., are "non-naturally occurring." In some embodiments, the variant subtilisin Carlsberg polypeptides described herein may be "full-length polypeptides" or "preproproteins" that include the signal peptide (amino acids 1-29 as set forth in SEQ ID NO:2), the pro-region (amino acids 30-105 as set forth in SEQ ID NO:2), and the mature protein or enzyme (amino acids 106-379 as set forth in SEQ ID NO:2) as shown in FIG. 1B. In alternative embodiments, the variant subtilisin Carlsberg polypeptides described herein may be "processed fragments" that include the pro-region and the mature protein or enzyme but not the signal peptide (the "proprotein"; SEQ ID NO: 27; FIG. 1C), or just include the mature protein or enzyme and not the signal peptide or the pro-region (the "mature protein" or "mature enzyme"; SEQ ID NO: 28; FIG. 1D).

In some embodiments, the present disclosure provides a nucleic acid molecule (for example, as set forth in SEQ ID NO: 1) encoding a variant subtilisin Carlsberg polypeptide, from *Bacillus licheniformis*, or a processed fragment thereof, the nucleic acid molecule further including a mutation at one or more of the codons corresponding to positions K88, D180, N181, N265, L321, L339 or Q379. In some embodiments, the mutations do not include the combination of the codons corresponding to positions D180, N265, and L321. In some embodiments, the mutations may result in an amino acid change to one or more of K88N, D180G, N181Y, N265S, L321F, L339M, or Q379P. In some embodiments, the present disclosure provides a nucleic acid molecule having at least 80% sequence identity, for example at least 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO: 1 or a processed fragment thereof and including a mutation at one or more of the codons corresponding to positions K88, D180, N181, N265, L321, L339 or Q379 of a subtilisin Carlsberg polypeptide, from *Bacillus licheniformis*, where the mutations do not include the combination of the codons corresponding to positions D180, N265, and L321.

In some embodiments, the present disclosure provides a variant subtilisin Carlsberg polypeptide, from *Bacillus licheniformis*, as set out in GenBank No. AGN35600 (for example, as set forth in SEQ ID NO: 2), or a processed fragment thereof, which further includes a mutation at one or more of positions K88, D180, N181, N265, L321, L339 or Q379. In some embodiments, the mutations do not include the combination of the amino acids at positions D180, N265, and L321. In some embodiments, the mutations may be one or more of K88N, D180G, N181Y, N265S, L321F, L339M, or Q379P. In some embodiments, the present disclosure provides a polypeptide having at least 80% sequence identity, for example at least 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO: 2 or a processed fragment thereof and including a mutation at one or more of positions corresponding to K88, D180, N181, N265, L321, L339 or Q379 of a subtilisin Carlsberg polypeptide, from *Bacillus licheniformis*, where the mutations do not include the combination of the amino acids at positions D180, N265, and L321.

In some embodiments, the present disclosure provides a nucleic acid molecule (SEQ ID NO: 1) encoding a variant subtilisin Carlsberg polypeptide, from *Bacillus licheniformis*, or a processed fragment thereof, the nucleic acid molecule further including a mutation at the codon corresponding to position K88. In some embodiments, the mutation may result in an amino acid change to K88N.

In some embodiments, the present disclosure provides a variant subtilisin Carlsberg polypeptide, from *Bacillus licheniformis*, as set out in GenBank No. AGN35600 (SEQ ID NO: 2), or a processed fragment thereof, which further includes a mutation at K88. In some embodiments, the mutation may be K88N.

In some embodiments, the present disclosure provides a nucleic acid molecule (SEQ ID NO: 1) encoding a variant subtilisin Carlsberg polypeptide, from *Bacillus licheniformis*, or a processed fragment thereof, the nucleic acid molecule further including a mutation at the codon corresponding to position D180. In some embodiments, the mutation may result in an amino acid change to D180G.

In some embodiments, the present disclosure provides a variant subtilisin Carlsberg polypeptide, from *Bacillus licheniformis*, as set out in GenBank No. AGN35600 (SEQ ID NO: 2), or a processed fragment thereof, which further includes a mutation at D180. In some embodiments, the mutation may be D180G.

In some embodiments, the present disclosure provides a nucleic acid molecule (SEQ ID NO: 1) encoding a variant subtilisin Carlsberg polypeptide, from *Bacillus licheniformis*, or a processed fragment thereof, the nucleic acid molecule further including a mutation at the codon corresponding to position N181. In some embodiments, the mutation may result in an amino acid change to N181Y.

In some embodiments, the present disclosure provides a variant subtilisin Carlsberg polypeptide, from *Bacillus licheniformis*, as set out in GenBank No. AGN35600 (SEQ ID NO: 2), or a processed fragment thereof, which further includes a mutation at N181. In some embodiments, the mutation may be N181Y.

In some embodiments, the present disclosure provides a nucleic acid molecule (SEQ ID NO: 1) encoding a variant subtilisin Carlsberg polypeptide, from *Bacillus licheniformis*, or a processed fragment thereof, the nucleic acid molecule further including a mutation at the codon corresponding to position N265. In some embodiments, the mutation may result in an amino acid change to N265S.

In some embodiments, the present disclosure provides a variant subtilisin Carlsberg polypeptide, from *Bacillus licheniformis*, as set out in GenBank No. AGN35600 (SEQ ID NO: 2), or a processed fragment thereof, which further includes a mutation at N265. In some embodiments, the mutation may be N265S.

In some embodiments, the present disclosure provides a nucleic acid molecule (SEQ ID NO: 1) encoding a variant subtilisin Carlsberg polypeptide, from *Bacillus licheniformis*, or a processed fragment thereof, the nucleic acid molecule further including a mutation at the codon corresponding to position L321. In some embodiments, the mutation may result in an amino acid change to L321F.

In some embodiments, the present disclosure provides a variant subtilisin Carlsberg polypeptide, from *Bacillus licheniformis*, as set out in GenBank No. AGN35600 (SEQ ID NO: 2), or a processed fragment thereof, which further includes a mutation at L321. In some embodiments, the mutation may be L321F.

In some embodiments, the present disclosure provides a nucleic acid molecule (SEQ ID NO: 1) encoding a variant subtilisin Carlsberg polypeptide, from *Bacillus licheniformis*, or a processed fragment thereof, the nucleic acid molecule further including a mutation at the codon corresponding to position L339. In some embodiments, the mutation may result in an amino acid change to L339M.

In some embodiments, the present disclosure provides a variant subtilisin Carlsberg polypeptide, from *Bacillus licheniformis*, as set out in GenBank No. AGN35600 (SEQ ID NO: 2), or a processed fragment thereof, which further includes a mutation at L339. In some embodiments, the mutation may be L339M.

In some embodiments, the present disclosure provides a nucleic acid molecule (SEQ ID NO: 1) encoding a variant subtilisin Carlsberg polypeptide, from *Bacillus licheniformis*, or a processed fragment thereof, the nucleic acid molecule further including a mutation at the codon corresponding to position Q379. In some embodiments, the mutation may result in an amino acid change to Q379P.

In some embodiments, the present disclosure provides a variant subtilisin Carlsberg polypeptide, from *Bacillus*

*licheniformis*, as set out in GenBank No. AGN35600 (SEQ ID NO: 2), or a processed fragment thereof, which further includes a mutation at Q379. In some embodiments, the mutation may be Q379P.

In some embodiments, the present disclosure provides a variant subtilisin Carlsberg polypeptide from *Bacillus licheniformis*, as set out in GenBank No. AGN35600 (SEQ ID NO: 2), or a processed fragment thereof, which includes mutations at the following residues: L339 and Q379.

In some embodiments, the present disclosure provides a variant subtilisin Carlsberg polypeptide from *Bacillus licheniformis*, as set out in GenBank No. AGN35600 (SEQ ID NO: 2), or a processed fragment thereof, which includes mutations at the following residues: D180 and L339.

In some embodiments, the present disclosure provides a variant subtilisin Carlsberg polypeptide from *Bacillus licheniformis*, as set out in GenBank No. AGN35600 (SEQ ID NO: 2), or a processed fragment thereof, which includes mutations at the following residues: D180 and Q379.

In some embodiments, the present disclosure provides a variant subtilisin Carlsberg polypeptide ("Subtilisin Carlsberg variant B24," "subtilisin B24," "variant B24," "B24 variant" or "B24"), from *Bacillus licheniformis*, as set out in GenBank No. AGN35600 (SEQ ID NO: 2), or a processed fragment thereof, which further includes mutations at the following residues: D180, L339, and Q379.

In some embodiments, the Subtilisin Carlsberg variant B24 or a processed fragment thereof, includes the following mutations: D180G, L339M, and Q379P (SEQ ID NOs: 9, 10, 23, 24, 25, or 26).

In some embodiments, the Subtilisin Carlsberg variant B24 (variant B24-G180A) includes the following mutations: D180A, L339M, and Q379P (SEQ ID NO: 13 or 14 or a processed fragment thereof).

In some embodiments, the Subtilisin Carlsberg variant (variant B24-G180D) includes the following mutations: L339M and Q379P (SEQ ID NO: 11 or 12 or a processed fragment thereof).

In some embodiments, the present disclosure provides a nucleic acid molecule encoding the Subtilisin Carlsberg variant polypeptide (variant B24-G180D) which includes the following mutations: L339M and Q379P (SEQ ID NO: 11 or 12 or a processed fragment thereof). In some embodiments, the present disclosure provides a nucleic acid molecule as set forth in SEQ ID NO: 5 or 6 or a processed fragment thereof. In some embodiments, the present disclosure provides a polypeptide encoded by SEQ ID NO: 5 or 6 or a processed fragment thereof.

In some embodiments, the present disclosure provides a nucleic acid molecule encoding the Subtilisin Carlsberg variant B24 polypeptide or a processed fragment thereof which includes mutations at the following residues: D180, L339, and Q379.

In some embodiments, the present disclosure provides a nucleic acid molecule encoding the Subtilisin Carlsberg variant B24 polypeptide which includes the following mutations: D180G, L339M, and Q379P (SEQ ID NO: 9, 10, 23, 24, 25, 26). In some embodiments, the present disclosure provides a nucleic acid molecule as set forth in SEQ ID NO: 3 or 4 or a processed fragment thereof. In some embodiments, the present disclosure provides a polypeptide encoded by SEQ ID NO: 3 or 4 or a processed fragment thereof.

In some embodiments, the present disclosure provides a nucleic acid molecule encoding the Subtilisin Carlsberg variant B24 polypeptide (variant B24-G180A) which includes the following mutations: D180A, L339M, and Q379P (SEQ ID NO: 13 or 14 or a processed fragment thereof). In some embodiments, the present disclosure provides a nucleic acid molecule as set forth in SEQ ID NO: 7 or 8 or a processed fragment thereof. In some embodiments, the present disclosure provides a polypeptide encoded by SEQ ID NO: 7 or 8 or a processed fragment thereof.

In some embodiments, the present disclosure provides a variant subtilisin Carlsberg polypeptide from *Bacillus licheniformis*, as set out in GenBank No. AGN35600 (SEQ ID NO: 2), or a processed fragment thereof which further includes mutations at the following residues: K88, D180, N181, N265, and L321 or combinations thereof, such as K88 and D180; K88 and N181; K88 and N265; K88 and L321; D180 and N181; D180 and N265; D180 and L321; N181 and N265; N181 and L321; K88, D180, and N181; K88, D180, and N265; K88, D180, and L321; D180, N181, and N265; D180, N265, and L321; N181, N265, and L321; K88, D180, N181, N265, and L321; etc.

In some embodiments, the present disclosure provides a variant subtilisin Carlsberg polypeptide ("Subtilisin Carlsberg variant P23," "subtilisin P23," "variant P23," or "P23"), from *Bacillus licheniformis*, as set out in GenBank No. AGN35600 (SEQ ID NO: 2), or a processed fragment thereof which further includes mutations at the following residues: K88, D180, N181, N265, and L321.

In some embodiments, the Subtilisin Carlsberg variant P23 includes the following mutations: K88N, D180G, N181Y, N265S, and L321F (SEQ ID NO: 17 or 18 or a processed fragment thereof).

In some embodiments, the present disclosure provides a nucleic acid molecule encoding the Subtilisin Carlsberg variant P23 polypeptide or a processed fragment thereof which includes mutations at the following residues: K88, D180, N181, N265, and L321.

In some embodiments, the present disclosure provides a nucleic acid molecule encoding the Subtilisin Carlsberg variant P23 polypeptide which includes the following mutations: K88N, D180G, N181Y, N265S, and L321F (SEQ ID NO: 17 or 18 or a processed fragment thereof). In some embodiments, the present disclosure provides a nucleic acid molecule as set forth in SEQ ID NO: 15 or 16 or a processed fragment thereof. In some embodiments, the present disclosure provides a polypeptide encoded by SEQ ID NO: 15 or 16 or a processed fragment thereof.

It is well known in the art that some modifications and changes can be made in the structure of a polypeptide without substantially altering the biological function of that peptide, to obtain a biologically equivalent polypeptide. In one aspect of the invention, variant subtilisin Carlsberg polypeptides also extend to biologically equivalent peptides that differ from a portion of the sequence of the variant subtilisin Carlsberg polypeptides by conservative amino acid substitutions that retain protease activity but do not affect the other properties (e.g., heat lability and/or lack of cold adaptation) of the variant subtilisin Carlsberg polypeptides described herein. Accordingly, in some embodiments, the present disclosure provides variant subtilisin Carlsberg polypeptides and nucleic acid molecules or a fragment thereof, for example, a processed fragment, that include mutations at one or more of positions K88, D180, N181, N265, L321, L339 or Q379 and may further include conservative substitutions or other mutations, where the conservative substitutions or other mutations retain protease activity but do not affect the other properties (e.g., heat lability and/or lack of cold adaptation). Such polypeptides and nucleic acid molecules may have at least 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO: 1 or SEQ ID NO: 2, or a fragment thereof, as appropriate.

As used herein, the term "conserved amino acid substitutions" refers to the substitution of one amino acid for another at a given location in a polypeptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the polypeptide by routine testing.

As used herein, the term "amino acids" means those L-amino acids commonly found in naturally occurring proteins, D-amino acids and such amino acids when they have been modified. Accordingly, amino acids of the invention may include, for example: 2-Aminoadipic acid; 3-Aminoadipic acid; beta-Alanine; beta-Aminopropionic acid; 2-Aminobutyric acid; 4-Aminobutyric acid; piperidinic acid; 6-Aminocaproic acid; 2-Aminoheptanoic acid; 2-Aminoisobutyric acid; 3-Aminoisobutyric acid; 2-Aminopimelic acid; 2,4 Diaminobutyric acid; Desmosine; 2,2'-Diaminopimelic acid; 2,3-Diaminopropionic acid; N-Ethylglycine; N-Ethylasparagine; Hydroxylysine; allo-Hydroxylysine; 3-Hydroxyproline; 4-Hydroxyproline; Isodesmosine; allo-Isoleucine; N-Methylglycine; sarcosine; N-Methylisoleucine; 6-N-methyllysine; N-Methylvaline; Norvaline; Norleucine; and Ornithine.

In some embodiments, conserved amino acid substitutions may be made where an amino acid residue is substituted for another having a similar hydrophilicity value (e.g., within a value of plus or minus 2.0, or plus or minus 1.5, or plus or minus 1.0, or plus or minus 0.5), where the following may be an amino acid having a hydropathic index of about −1.6 such as Tyr (−1.3) or Pro (−1.6) are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative embodiments, conservative amino acid substitutions may be made where an amino acid residue is substituted for another having a similar hydropathic index (e.g., within a value of plus or minus 2.0, or plus or minus 1.5, or plus or minus 1.0, or plus or minus 0.5). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In alternative embodiments, conservative amino acid substitutions may be made using publicly available families of similarity matrices (Altschul, S. F. 1991. "Amino acid substitution matrices from an information theoretic perspective." Journal of Molecular Biology, 219: 555-665; Dayhoff, M. O., Schwartz, R. M., Orcutt, B. C. 1978. "A model of evolutionary change in proteins." In "Atlas of Protein Sequence and Structure" 5(3) M. O. Dayhoff (ed.), 345-352, National Biomedical Research Foundation, Washington; States, D. J., Gish, W., Altschul, S. F. 1991. "Improved Sensitivity of Nucleic Acid Database Search Using Application-Specific Scoring Matrices" Methods: A companion to Methods in Enzymology 3(1): 66-77; Steven Henikoff and Jorja G. Henikoff. 1992 "Amino acid substitution matrices from protein blocks." Proc. Natl. Acad. Sci. USA. 89(biochemistry): 10915-10919; M. S. Johnson and J. P. Overington. 1993. "A Structural Basis of Sequence Comparisons: An evaluation of scoring methodologies." Journal of Molecular Biology. 233: 716-738. Steven Henikoff and Jorja G. Henikoff. 1993. "Performance Evaluation of Amino Acid Substitution Matrices." Proteins: Structure, Function, and Genetics. 17: 49-61; Karlin, S. and Altschul, S. F. 1990. "Methods for assessing the statistical significance of molecular sequence features by using general scoring schemes" Proc. Natl. Acad. Sci. USA. 87: 2264-2268.) The PAM matrix is based upon counts derived from an evolutionary model, while the Blosum matrix uses counts derived from highly conserved blocks within an alignment. A similarity score of above zero in either of the PAM or Blosum matrices may be used to make conservative amino acid substitutions.

In alternative embodiments, conservative amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

Conservative amino acid changes can include the substitution of an L-amino acid by the corresponding D-amino acid, by a conservative D-amino acid, or by a naturally-occurring, non-genetically encoded form of amino acid, as well as a conservative substitution of an L-amino acid. Naturally-occurring non-genetically encoded amino acids include beta-alanine, 3-amino-propionic acid, 2,3-diamino propionic acid, alpha-aminoisobutyric acid, 4-amino-butyric acid, N-methylglycine (sarcosine), hydroxyproline, ornithine, citrulline, t-butylalanine, t-butylglycine, N-methylisoleucine, phenylglycine, cyclohexylalanine, norleucine, norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, homoarginine, N-acetyl lysine, 2-amino butyric acid, 2-amino butyric acid, 2,4,-diamino butyric acid, p-aminophenylalanine, N-methylvaline, homocysteine, homoserine, cysteic acid, epsilon-amino hexanoic acid, delta-amino valeric acid, or 2,3-diaminobutyric acid.

In alternative embodiments, conservative amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (*J. Mol. Bio.* 179:125-142, 184). Genetically encoded hydrophobic amino acids include Gly, Ala, Phe, Val, Leu, Ile, Pro, Met and Trp, and genetically encoded hydrophilic amino acids include Thr, His, Glu, Gln, Asp, Arg, Ser, and Lys. Non-genetically encoded hydrophobic amino acids include t-butylalanine, while non-genetically encoded hydrophilic amino acids include citrulline and homocysteine.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR, etc., where R is independently (C$_1$-C$_6$) alkyl, substituted (C$_1$-C$_6$) alkyl, (C$_1$-C$_6$) alkenyl, substituted (C$_1$-C$_6$) alkenyl, (C$_1$-C$_6$) alkynyl, substituted (C$_1$-C$_6$) alkynyl, (C$_5$-C$_{20}$) aryl, substituted (C$_5$-C$_{20}$) aryl, (C$_6$-C$_{26}$) alkaryl, substituted (C$_6$-C$_{26}$) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe, Tyr, and Trp, while non-genetically encoded aromatic amino acids include phenylglycine, 2-napthylalanine, beta-2-thienylalanine, 1,2,3,4-tetrahydro-isoquinoline-3-carboxylic acid, 4-chlorophenylalanine, 2-fluorophenylalanine3-fluorophenylalanine, and 4-fluorophenylalanine.

An apolar amino acid is a hydrophobic amino acid with a side chain that is uncharged at physiological pH and which has bonds in which a pair of electrons shared in common by two atoms is generally held equally by each of the two atoms (i.e., the side chain is not polar). Genetically encoded apolar amino acids include Gly, Leu, Val, Ile, Ala, and Met, while non-genetically encoded apolar amino acids include cyclohexylalanine. Apolar amino acids can be further subdivided to include aliphatic amino acids, which is a hydrophobic amino acid having an aliphatic hydrocarbon side chain. Genetically encoded aliphatic amino acids include Ala, Leu, Val, and Ile, while non-genetically encoded aliphatic amino acids include norleucine.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln, while non-genetically encoded polar amino acids include citrulline, N-acetyl lysine, and methionine sulfoxide.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His, while non-genetically encoded basic amino acids include the non-cyclic amino acids ornithine, 2,3,-diaminopropionic acid, 2,4-diaminobutyric acid, and homoarginine.

It will be appreciated by one skilled in the art that the above classifications are not absolute and that an amino acid may be classified in more than one category. In addition, amino acids can be classified based on known behaviour and or characteristic chemical, physical, or biological properties based on specified assays or as compared with previously identified amino acids. Amino acids can also include bifunctional moieties having amino acid-like side chains.

Conservative changes can also include the substitution of a chemically derivatised moiety for a non-derivatised residue, by for example, reaction of a functional side group of an amino acid. Thus, these substitutions can include compounds whose free amino groups have been derivatised to amine hydrochlorides, p-toluene sulfonyl groups, carbobenzoxy groups, t-butyloxycarbonyl groups, chloroacetyl groups or formyl groups. Similarly, free carboxyl groups can be derivatized to form salts, methyl and ethyl esters or other types of esters or hydrazides, and side chains can be derivatized to form O-acyl or O-alkyl derivatives for free hydroxyl groups or N-im-benzylhistidine for the imidazole nitrogen of histidine. Peptide analogues also include amino acids that have been chemically altered, for example, by methylation, by amidation of the C-terminal amino acid by an alkylamine such as ethylamine, ethanolamine, or ethylene diamine, or acylation or methylation of an amino acid side chain (such as acylation of the epsilon amino group of lysine). Peptide analogues can also include replacement of the amide linkage in the peptide with a substituted amide (for example, groups of the formula —C(O)—NR, where R is (C$_1$-C$_6$) alkyl, (C$_1$-C$_6$) alkenyl, (C$_1$-C$_6$) alkynyl, substituted (C$_1$-C$_6$) alkyl, substituted (C$_1$-C$_6$) alkenyl, or substituted (C$_1$-C$_6$) alkynyl) or isostere of an amide linkage (for example, —CH$_2$NH—, —CH$_2$S, —CH$_2$CH$_2$—, —CH=CH— (cis and trans), —C(O)CH$_2$—, —CH(OH)CH$_2$—, or —CH$_2$SO—). The nucleic acid sequences, as described herein, may be recombinant sequences. The term "recombinant" means that something has been recombined, so that when made in reference to a nucleic acid construct the term refers to a molecule that is comprised of nucleic acid sequences that are joined together or produced by means of molecular biological techniques. The term "recombinant" when made in reference to a protein or a polypeptide refers to a protein or polypeptide molecule which is expressed using a recombinant nucleic acid construct created by means of molecular biological techniques. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as 'recombinant' therefore indicates that the nucleic acid molecule has been manipulated using genetic engineering, i.e. by human intervention. Recombinant nucleic acid constructs may for example be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

The nucleic acid or polypeptide molecules, as described herein, may be "isolated" i.e., separated from the components that naturally accompany it. Typically, a molecule is isolated when it is at least 70%, 75%, 80%, or 85%, or over 90%, 95%, or 99% by weight, of the total material in a sample. Thus, for example, a polypeptide that is chemically synthesised, produced by recombinant technology, isolated by known purification techniques or as described herein, will be generally be substantially free from its naturally associated components. An isolated molecule can be obtained, for example, by extraction from a natural source that has been subjected to, for example, mutagenesis techniques as described herein or known in the art; by expression of a recombinant nucleic acid molecule encoding a polypeptide compound; or by chemical synthesis. The degree of isolation or purity can be measured using any appropriate method such as column chromatography, gel electrophoresis, HPLC, etc. A nucleic acid molecule is "isolated" when it is not immediately contiguous with (i.e., covalently linked to) the coding sequences with which it is normally contiguous in the naturally occurring genome of the organism from which the DNA of the invention is derived. Therefore, an "isolated" nucleic acid molecule is intended to mean a nucleic acid molecule which is not flanked by nucleic acid molecules which normally (in nature) flank the gene or nucleic acid molecule (such as in genomic sequences) and/or has been completely or partially purified from other transcribed sequences (as in a cDNA or RNA library). For example, an isolated nucleic acid molecule may be substantially isolated with respect to the complex cellular milieu in which it naturally occurs. In some instances, the isolated material will form part of a composition (for example, a crude extract containing other substances), buffer system or reagent mix. In other circumstance, the material may be purified to essential homogeneity, for example as determined by PAGE or column chromatography such as HPLC. The term therefore includes, e.g., a recombinant nucleic acid incorporated into a vector, such as an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. Preferably, an isolated nucleic acid comprises at least about 70%, 80%, 90%, 95%, or 99% (on a molar basis) of all macromolecular species present. Thus, an isolated nucleic acid molecule can include a nucleic acid molecule which is synthesized chemically or by recombinant means. Recombinant DNA contained in a vector are included in the definition of "isolated" as used herein. Also, isolated nucleic acid molecules include recombinant DNA molecules in heterologous host cells, as well as partially or substantially purified DNA molecules in solution.

Polypeptides, peptides or analogues thereof can be synthesised by standard chemical techniques, for example, by automated synthesis using solution or solid phase synthesis methodology. Automated peptide synthesisers are commercially available and use techniques well known in the art. Polypeptides, peptides or analogues thereof can also be prepared using recombinant DNA technology using standard methods such as those described in, for example, Sambrook, et al. (Molecular Cloning: A Laboratory Manual. $2^{nd}$ ed., Cold Spring Harbor Laboratory, Cold Spring Harbor Laboratory Press, Cold Spring Harbor, N.Y., 1989) or Ausubel et al. (Current Protocols in Molecular Biology, John Wiley & Sons, 1994).

In some embodiments, the variant polypeptides may include additional sequences that, for example, assist in purification. For example, the variant polypeptides may include polyhistidine tags, epitope tags, FLAG tags, or GST sequences, as described herein or known in the art.

The variant polypeptides (such as variant B24 or P23) or fragments thereof can be prepared employing standard methods in molecular biology and biochemistry. For example, a plasmid or suitable vector expressing a variant polypeptide (an "expression vector") can be transformed into a suitable host cell. A suitable vector can include, without limitation, a plasmid, a cosmid, a phage, a virus, a bacterial artificial chromosome (BAC), a yeast artificial chromosome (YAC), etc., into which a nucleic acid sequence, as described herein, can be inserted such that a variant polypeptide, as described herein, is expressed by a suitable host cell. The vector may include regulatory sequences, such as a promoter, enhancer, etc. and/or selectable markers, such as those that confer antibiotic resistance. Suitable vectors are commercially available or known in the art.

Suitable host cells can include, without limitation, bacterial (e.g., *E. coli, Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, Bacillus thuringiensis, Streptomyces achromogenes, Streptomyces avermitilis, Streptomyces coelicolor, Streptomyces griseus, Streptomyces lividans, Salmonella typhimurium*, etc.), fungal (e.g., *Saccharomyces cerevisiae, Pichia pastoris*, or *Neurospora crassa*), plant, insect (e.g., *Drosophila* or *Spodoptera frugiperda*) or other animal cells, as long as they are capable of expressing functional (e.g., heat labile) variant polypeptides as described herein. Host cells can be cultured in conventional nutrient media modified as appropriate for activating promoters, selecting transformants, or expressing the variant polypeptides as known in the art or described herein.

In some embodiments, a strain of *Bacillus subtilis* that has been engineered to delete five of the seven genes that encode secreted proteases can be used. Such a strain can be obtained, for example, from the *Bacillus* Genetic Stock Center (BGSC code 1A1097; Doi R H, He X S, McCready P, Bakheit N. *Bacillus subtilis*: a model system for heterologous gene expression. in Applications of Enzyme Biotechnology. eds Kelly J W, Baldwin T O (Plenum Press, New York, N.Y.), pp 261-272). In such a strain the variant polypeptide is the dominant secreted protease and one of the few secreted proteins that is found in the culture supernatant. The variant polypeptide-expressing strain is grown at 31° C. in LB broth (10 gm/L tryptone; 5 gm/L yeast extract; 5 gm/L NaCl) to late stationary phase. The cells in the culture are removed by centrifugation or tangential flow filtration. If centrifugation is used the culture supernatant is cleared by filtration through a 0.22 μm filter. The cleared supernatant is applied to a column containing HIS-Select™ Nickel Affinity Gel-SIGMA. Before the cleared supernatant is applied the affinity gel is washed with 2 column volumes of deionized water to remove the 20% ethanol storage buffer and then equilibrated with 3 column volumes of equilibration buffer (100 mM HEPES [pH 7.5], 10 mM imidazole, 100 mM NaCl, 10 mM $CaCl_2$). The clarified crude lysate is loaded onto the column at a flow rate of ~2 column volumes/hour. The flow-through is collected in fractions and each fraction is collected for 5 minutes. The column is then washed with wash buffer (100 mM HEPES [pH 7.5], 10 mM imidazole, 100 mM NaCl, 10 mM $CaCl_2$) at a flow rate of ~10 column volumes/hour until the $A_{280}$ reaches the same $A_{280}$ as the wash buffer. The His-tagged B24 protease is eluted from the column using elution buffer (100 mM HEPES [pH 7.5], 150 mM imidazole, 100 mM NaCl, 10 mM $CaCl_2$) at a flow rate of 3 column volumes/hour until the $A_{280}$ reaches the same $A_{280}$ as the elution buffer. Fractions containing protease activity are pooled, dialyzed to remove the imidazole and lyophilized.

In general, a variant subtilisin Carlsberg polypeptide according to the present disclosure is heat-labile. By "heat-labile" is meant a polypeptide that exhibits substantial loss of activity, for example, protease activity, upon exposure to temperatures over about 50° C. for at least 10 minutes. In some embodiments, a heat-labile variant polypeptide as described herein exhibits substantial loss of activity at temperatures over about 50° C., such as about 55° C., 60° C., 65° C., 70° C. or 80° C., or any value between about 50° C. and about 80° C., or over about 80° C., for at least about 10 minutes, such as about 15, 20, 30, or 45 minutes, or any value between about 10 minute or about 45 minutes, or more. In some embodiments, a heat-labile polypeptide as described herein (such as the B24 variant at a concentration of 100 μg/ml (micrograms/ml)) exhibits >95% loss of its activity in 45 minutes upon heating to 50° C.; or in 30 minutes upon heating to 60° C.; or in 20 min upon heating to 65° C.; or in 15 minutes upon heating to 70° C.; or in 10 min upon heating to 80° C.

In some embodiments, a heat-labile polypeptide according to the present disclosure may be a polypeptide that exhibits substantial loss of activity upon exposure to temperatures at which other molecules (e.g., DNA, RNA, polypeptides, small molecules) are stable and/or do not exhibit loss of activity. For example, in some embodiments, a heat-labile polypeptide according to the present disclosure may exhibit loss of activity at a temperature sufficient to preserve DNA in a double-stranded form.

It is to be understood that full or 100% loss of activity is not required and that parameters such as the pH, target substrate, and the concentration of the variant polypeptide can affect its activity. Accordingly, in some embodiments, substantial loss of activity can be determined according to standard techniques, depending on such parameters. In alternative embodiments, a substantial loss of activity can include about 50% to about 100% loss of activity, or any value therebetween, such as about 55%, 60%, 65%, 70%, 75%, 80%, 85%, 90%, 95%, or 99% loss of activity.

In some embodiments, a variant subtilisin Carlsberg polypeptide according to the present disclosure exhibits optimal activity at temperatures of about 20° C. to about 40° C., or any value therebetween, such as about 20° C., 25° C., 30° C., 35° C., 37° C., 40° C., etc. In some embodiments, a variant subtilisin Carlsberg polypeptide according to the present disclosure exhibits optimal activity at about 37° C.

In general, a variant subtilisin Carlsberg polypeptide according to the present disclosure may be used in any application in which heat-lability is useful. For example, variant subtilisin Carlsberg polypeptide according to the present disclosure may be used to digest or degrade a target polypeptide present in a sample, under conditions suitable for protease activity of the variant polypeptide. After digestion or degradation of the target polypeptide has proceeded to the extent determined to be sufficient under the specific circumstances, the variant subtilisin Carlsberg polypeptide may be inactivated by increasing the temperature of the sample. A "target polypeptide" may include, without limitation, an enzyme, a nuclease, or any other protein, polypeptide, or proteinaceous material that needs to be removed. By "removal" of a target polypeptide is meant removal, reduction and/or inactivation of the target polypeptide by, for example, digestion or degradation by a protease. It is to be understood that 100% removal is not always required and therefore a target polypeptide may be considered sufficiently removed if the amount or activity of the target polypeptide is reduced by at least 10%, 20%, 30%, 40%, 50%, 60%, 70%, 80%, 90%, 95%, or 99%, after treatment with a protease, compared to its amount or activity prior to treatment. A sample may be any material from which removal of a target polypeptide is desired, for example, a molecular biology sample, a clinical sample, a diagnostic sample, a forensic sample, etc.

In some embodiments, a variant subtilisin Carlsberg polypeptide according to the present disclosure may be used to digest molecular biology enzymes and/or other proteins in a DNA manipulation technique or any technique that requires the removal of a protein, followed by a moderate heat inactivation step.

In some embodiments, a variant subtilisin Carlsberg polypeptide according to the present disclosure may be used to digest molecular biology enzymes, for example, heat resistant enzymes such as Taq polymerase and the heat resistant restriction enzyme PvuII.

In some embodiments, a variant subtilisin Carlsberg polypeptide according to the present disclosure may be used to remove contaminating DNA degrading nucleases, DNA modifying enzymes and/or other proteins from a preparation of plasmid DNA isolated from *Escherichia coli*, such as a standard mini-preparation.

In some embodiments, a variant subtilisin Carlsberg polypeptide according to the present disclosure may be used to remove contaminating DNA degrading nucleases, DNA modifying enzymes and/or other proteins from a preparation of chromosomal DNA isolated from, for example, a microbial, plant, and/or animal cell.

In some embodiments, a variant subtilisin Carlsberg polypeptide according to the present disclosure may be used to remove contaminating DNA degrading nucleases, DNA modifying enzymes and/or other proteins from a preparation of mitochondrial DNA isolated from an animal cell.

In some embodiments, a variant subtilisin Carlsberg polypeptide according to the present disclosure may be used to remove contaminating proteins from a forensic sample or a clinical and/or diagnostic sample. For example, a variant subtilisin Carlsberg polypeptide according to the present disclosure may be used prior to probing the sample with an antibody, such as in a drug test, or prior to amplifying DNA, such as in a paternity test.

In some embodiments, a variant subtilisin Carlsberg polypeptide according to the present disclosure may be used to remove RNA degrading nucleases and/or RNA modifying enzymes from a preparation of RNA.

In some embodiments, a variant subtilisin Carlsberg polypeptide according to the present disclosure may be used in a process of making cDNA from mRNA. For example, a preparation of mixed nucleic acids may be treated with a DNase to remove contaminating DNA. A variant subtilisin Carlsberg polypeptide according to the present disclosure may then be added to remove the DNase, after which the polypeptide according to the present disclosure may be inactivated by exposing it to a temperature at which it exhibits heat lability. The cDNA may then be produced from the mRNA.

In some embodiments, a variant subtilisin Carlsberg polypeptide according to the present disclosure may be used to remove a restriction enzyme (e.g., AvrII, BamHI, BglII, DraIII, HpaI, KpnI, MfeI, PstI, PvuII, Tsp509I, etc.; see the New England Biolabs section Tools & Resources section relating to Heat Inactivation at https[://]www[.]neb[.]com/tools-and-resources/usage-guidelines/heat-inactivation, which lists a number of restriction enzymes that cannot be heat-inactivated) following digestion of DNA followed by heat inactivation of the polypeptide according to the present disclosure by exposing it to a temperature at which it exhibits heat lability. In some embodiments, a variant subtilisin Carlsberg polypeptide according to the present disclosure may be used to remove a restriction or other enzyme which cannot be inactivated using standard heat inactivation techniques.

In some embodiments, a variant subtilisin Carlsberg polypeptide according to the present disclosure may be used to remove a DNA modifying enzyme, such as alkaline phosphatase or T4 DNA kinase, followed by heat inactivation of the variant subtilisin Carlsberg polypeptide according to the present disclosure by exposing it to a temperature at which it exhibits heat lability.

In some embodiments, a variant subtilisin Carlsberg polypeptide according to the present disclosure may be used in the purification of proteins aggregated in inclusion bodies to remove contaminating proteins, followed by heat inactivation of the variant subtilisin Carlsberg polypeptide according to the present disclosure by exposing it to a temperature at which it exhibits heat lability.

In some embodiments, a variant subtilisin Carlsberg polypeptide according to the present disclosure may be used in the purification of a carbohydrate to remove contaminating proteins, followed by heat inactivation of the variant subtilisin Carlsberg polypeptide according to the present disclosure by exposing it to a temperature at which it exhibits heat lability, and then modification of the carbohydrate with an enzyme.

In some embodiments, a variant subtilisin Carlsberg polypeptide according to the present disclosure may be used in the purification of a lipid to remove contaminating proteins, followed by heat inactivation of the variant subtilisin Carlsberg polypeptide according to the present disclosure by exposing it to a temperature at which it exhibits heat lability, and then modification of the lipid with an enzyme.

In some embodiments, a variant subtilisin Carlsberg polypeptide according to the present disclosure can be used in an automated process that involves successive steps that use enzymes, so that the enzymes used in one step are removed by action of the polypeptide according to the present disclosure (e.g., protease action), followed by heat inactivation of the variant subtilisin Carlsberg polypeptide according to the present disclosure by exposing it to a temperature at which it exhibits heat lability, before the next step that involves the addition of another enzyme.

The variant subtilisin Carlsberg polypeptides may be provided in a suitable amount, sufficient to achieve a desired level of protease activity, in a composition that may also include a suitable carrier. The carrier may be, without limitation, any component used in molecular biology, forensic, cleaning or other compositions.

The composition may be a cleaning composition for, for example, cleaning fabrics, carpets, dishes, etc. The composition may be in any suitable form, such as a liquid, gel, granule, cake, bar, paste, powder, or spray. In some embodiments, the cleaning composition may be a detergent composition, such as a laundry detergent or a dish detergent. It is to be understood that a cleaning composition may include other components, such as surfactants, chelating agents, bleach, fabric conditioners, polyols, lactic acid, boric acid, etc.

The present invention will be further illustrated in the following examples.

EXAMPLES

Error-Prone PCR-Based Mutagenesis

Error-prone polymerase chain reaction (PCR)-based mutagenesis using *B. subtilis* as a host (Zhang, X-Z and Zhang Y-H. P. "Simple, fast and high-efficiency transformation system for directed evolution of cellulose in *Bacillus subtilis*, MicrobBiotechnol. 4(1): 98-105, 2011) was conducted and involved the following general steps: designing synthetic DNA and primers; generating a library of random DNA mutants with error prone PCR; multimerization of plasmids with overlap PCR; transforming the library into *B. subtilis*; and selecting for protein mutants.

Synthetic DNA and Primers

A synthetic gene with the sequence shown in FIG. 1A was obtained from Integrated DNA Technologies. The core of the sequence encodes a naturally occurring variation of subtilisin Carlsberg (subC) from the species *Bacillus licheniformis* (subtilisin Carlsberg AprE [*Bacillus licheniformis* 9945A]; GenBank: AGN35600). The 3' end was altered to add a histidine tag before the stop codon. The 3' and 5' ends of the sequence contain sequence overlaps from the vector pZY167 (Zyprian E, Matzura H., Characterization of signals promoting gene expression on the Staphylococcus aureus plasmid pUB110 and development of a gram-positive expression vector system. DNA. 1986 June; 5(3):219-25; PMID: 3013549) to allow for overlap PCR of the subtilisin gene with the plasmid.

The primers for amplifying the synthetic gene for cloning and subsequent error prone PCR were:

```
SubC-F:
                                (SEQ ID NO: 19)
TCAGCCCAAGCTTTCTAGAGTCCA,
and SubC-R:
                                (SEQ ID NO: 20)
GAATTCCCCGGATCCGTCAAC.
```

The primers for amplifying the vector pZY167 for creating plasmid multimers with the subtilisin gene via overlap PCR were:

```
167-S.CtoL:
                                (SEQ ID NO: 21)
ATCAATCTCCTATCCTATATGGACTCTAGAAAGCTTGGGCTGA
and 167-S.CtoR:
                                (SEQ ID NO: 22)
TGAGATCAACAGTTTGGGCAGTTGACGGATCCGGGGAATTC.
```

The synthetic gene was amplified by PCR and then joined to the vector pZY167 to generate the plasmid pZY167::subC.

Error Prone PCR

A randomly mutated library of subC was generated by error-prone PCR as follows. First, the synthetic subtilisin Carlsberg gene was amplified using the PrimeSTAR GXL polymerase. 2 µl of that reaction was used as template in a 100 µl PCR reaction using Mutazyme II polymerase (Agilent Technologies) using the manufacturer's protocol. The PCR amplicon was purified using a Nucleospin PCR cleanup column.

Plasmid Multimerization by Overlap PCR

The plasmid pZY167 was linearized by inverse PCR using the primers 167-S.CtoL and 167-S.CtoR. The linearized plasmid and error-prone PCR reaction products of subC were purified using a Nucleospin PCR cleanup column. The multimerization process was done according to Zhang and Zhang, supra, using template pZY167 at 0.15 ng/µl, the error-prone PCR product of the synthetic subtilisin C gene at 5 ng/µl, and PrimeSTAR GXL DNA polymerase to carry out the amplification.

Preparation and Transformation of *B. subtilis* Cells

The *B. subtilis* SCK6 strain was inoculated into 3 ml of LB medium with 1 µg/ml$^{-1}$ erythromycin in a test tube. The cells were cultivated at 37° C. with shaking at 200 rpm overnight (about 14 hours). The culture was then diluted to 1.0 $A_{600}$ in a fresh LB medium containing 1% (w/v) xylose and then grown for 2 hours. The resulting supercompetent cell culture was ready to be transformed. One microlitre of the PCR product containing plasmid multimers was mixed with 100 µl of the supercompetent cells in a plastic test tube and cultivated at 37° C. with shaking at 200 rpm for 90 min, then 100 µl aliquots were plated onto LB agar petri plates supplemented with 25 µg/ml of kanamycin sulfate and 1% skim milk powder (EMD Millipore).

Screening Colonies for Temperature Sensitive Protease

Out of approximately 800 colonies grown at 30° C., about 2% had active protease as determined by zones of clearing around the colonies. The milk plates were 1% skim milk powder (EMD Millipore) with 1.5% agar (Difco). Zones of clearing were circles of transparency created when active protease digests the milk, which creates a cloudy appearance to the plates. The 2% of clones with active protease were grown in 3 ml of LB broth with 25 µg/ml of kanamycin sulfate. Cells were pelleted, the supernatant containing unpurified protease was collected, and 50 µl aliquots were heat treated at 60° C. for 10 minutes; duplicate aliquots were kept at room temperature. The room temperature and the 60° C.-treated aliquots were screened for their ability to produce zones of clearing on milk agar plates. Subtilisin variants that could not be heat inactivated were discarded. Approximately 20% of these variants were heat inactivated, in that they did not produce a zone of clearing on milk plates after heat denaturation. Two of these variants (B24 and P23), with stable repeatable zones of clearing at room temperature and no activity after heat denaturation, were selected for sequencing and further characterization.

Subtilisin Carlsberg variant B24 had three amino acid changes at D180G, L339M, and Q379P. DNA sequences encoding heat-labile B24 variants of subtilisin are provided at FIGS. 2A-F.

Subtilisin Carlsberg variant P23 had five amino acid changes at K88N, D180G, N181Y, N265S, and L321F. The DNA sequence encoding P23 is provided at FIGS. 3A-B.

Figure 4B:
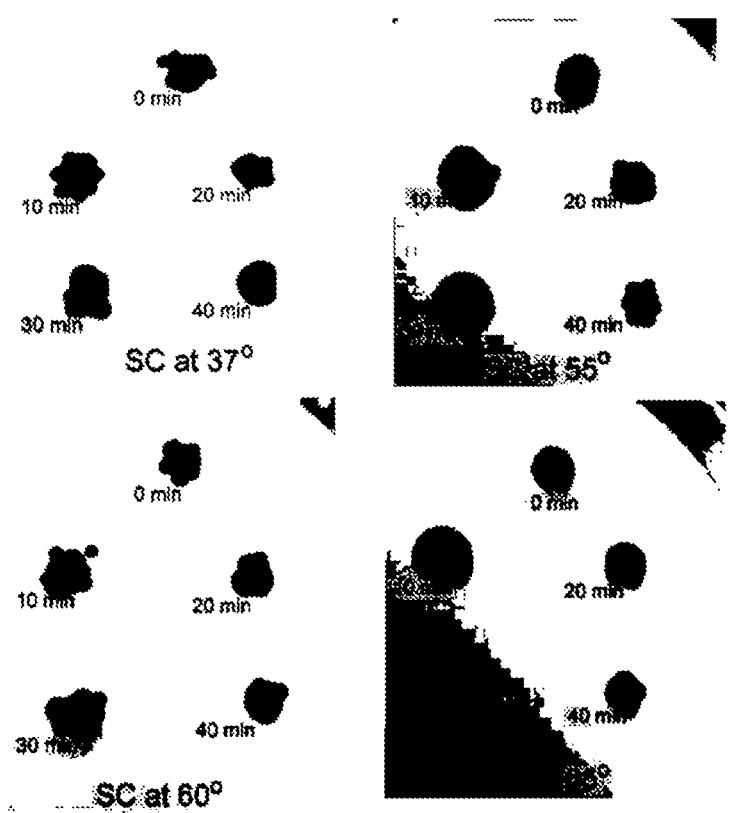
FIG. 4B is a photograph of heat stability of wild type subtilisin Carlsberg, compared to Subtilisin Carlsberg variant B24, at 55° C., 60° C. and 65° C. over 40 minutes. The experiments were done with purified enzyme.

Both variants lost protease activity after incubation at 60° C. for 10 minutes, as determined by the ability to produce zones of clearing on milk agar plates. Variant B24 was further characterized through a time course assay which confirmed loss of activity after a 10-minute incubation 60° C. (FIG. 4).

Subtilisin B24 Purification from Culture Supernatants

Figure 5:
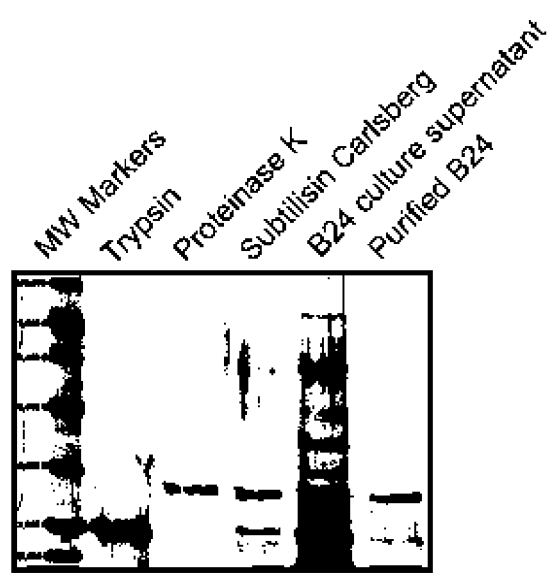
FIG. 5 is a gel showing the purification of the subtilisin B24 variant from culture supernatants.

The *Bacillus subtilis* strain 1A1097 (*Bacillus* Genetic Stock Center, Columbus, Ohio) harboring a plasmid encoding the gene encoding B24 was streaked out for individual colonies on a LB agar plate containing 30 µg/mL of kanamycin and 1% dry milk. After 24 hour of incubation at 30° C. 10 isolated colonies showing zones of clearing of the milk opacity were chosen and used to inoculate 1 L of LB media containing 30 µg/mL of kanamycin. The culture was grown at 30° C. for 40 hours, the cells were removed via centrifugation and the subtilisin B24 was purified from the supernatant. The supernatant was further cleared by passing it through a 0.2 µm filter. An aliquot was saved to compare the purity before and after purification. The filtered supernatant was mixed 50:50 with equilibration buffer (20 mM HEPES, 300 mM NaCl, 10 mM imidazole, pH 7.5) and applied to a (nickle nitrilotriacetic acid (Ni-NTA) column (Sigma). The column was washed with wash buffer (20 mM HEPES, 300 mM NaCl, 25 mM imidazole, pH 7.4) to remove any loosely bound contaminating proteins. The B24 protease was eluted using elution buffer (20 mM HEPES, 300 mM NaCl, 200 mM imidazole, pH 7.4) into 5 mL fractions. From each fraction 5 µl was spotted onto milk agar (1% milk, 1.5% agar) to test for protease activity, as evidenced by the clearing of the opacity created by the milk. Fractions with protease activity were pooled, and purified B24 and supernatant were loaded onto a 10% SDS-PAGE gel along with commercial trypsin, proteinase K, and subtilisin Carlsberg (FIG. 5). The gel was run at 200V for 45 minutes and stained using a silver staining method. The B24 supernatant (lane 5) contained multiple bands while the purified B24 (lane 6) contained two bands with one of the bands at the correct ~27 KDa molecular weight. The lower band is not considered contamination because the commercial subtilisin Carlsberg (lane 4) which is the parent protease, has the same banding pattern as the purified B24.

Figure 6:
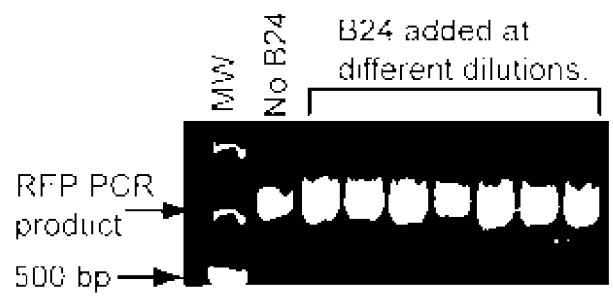
FIG. 6 is a gel showing that the purified subtilisin B24 preparation does not contain detectable amounts of DNases.

Purified subtilisin B24 was mixed with PCR amplicon of the red fluorescent protein gene (RFP) and was incubated for 1 h at 37° C. The incubated samples were loaded onto a 0.75% agarose gel containing Gel Red (FIG. 6). The gel was run at 70V for 2 hours. The bands were detected using UV light. The results indicated that incubation with subtilisin B24 did not lead to smearing or loss of PCR product. Therefore, purified subtilisin B24 did not contain DNases.

Figure 7:
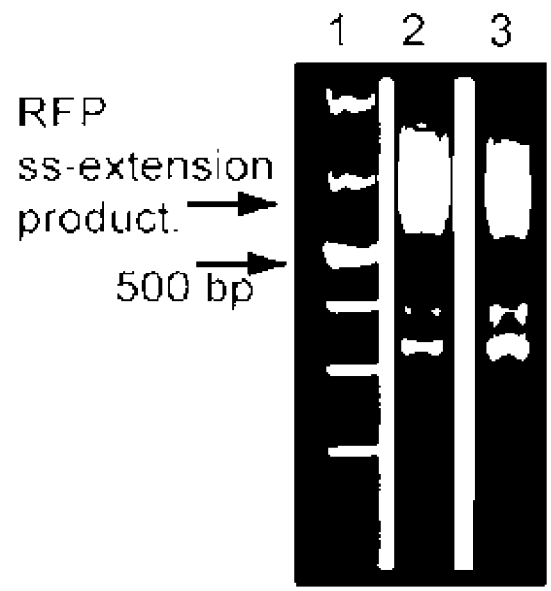
FIG. 7 is a gel showing that the purified subtilisin B24 preparation does not contain detectable amounts of single stranded DNA nucleases.

A single primer was used in 60 cycles of a mock PCR reaction to create single-stranded DNA. B24 was added to one sample (shown in lane 3) and incubated at 37° C. for 1 h (FIG. 7). The results indicated that incubation with subtilisin B24 did not lead to smearing or loss of single stranded DNA bands. Therefore, purified subtilisin B24 did not contain nucleases that attack single stranded DNA.

Heat Inactivation of Subtilisin B24 Compared to Proteinase K

Heat inactivation of subtilisin B24 was compared to proteinase K using a protease assay. The protease assay was conducted using the reagents supplied in a Pierce™ Fluorescent Protease Assay Kit (catalog number 23266). Solutions of the subtilisin B24 variant and proteinase K were made up to 1 mg/ml in a buffer of 25 mM Tris, 0.15M NaCl, at pH 7.2. To test sensitivity to heat, 100 µl aliquots of each protease were incubated at temperatures of 40° C., 50° C., 60° C. and 70° C., for 0, 10, 20, and 30 minutes. After incubation, each of the protease solutions were transferred to wells in a 96 well plate and mixed with 100 µl of FTC-Casein solution provided with the assay kit. The assay plate was incubated at room temperature for 5 minutes and fluorescence read with a Molecular Devices Spectra Max M5 plate reader with the filters for excitation and emission set at 485 nm and 538 nm respectively.

Figure 8:
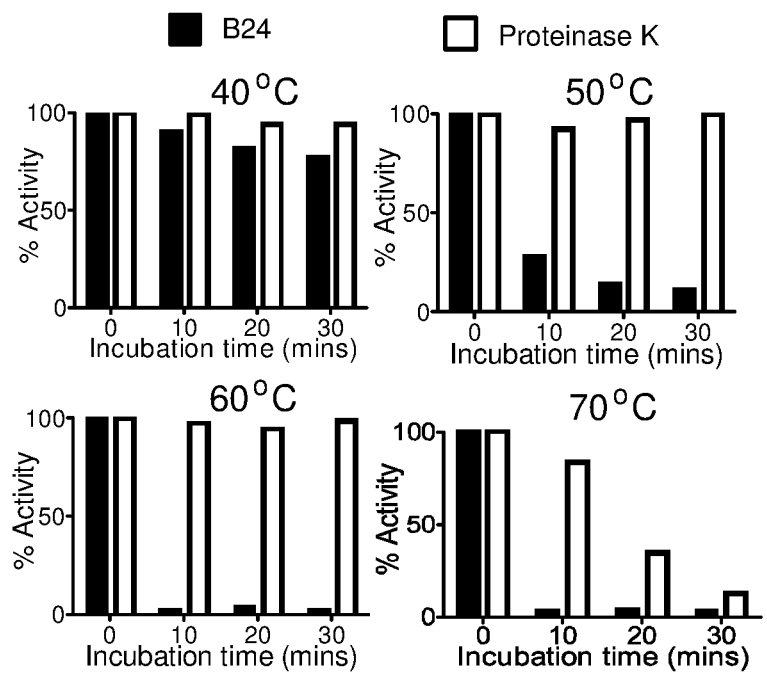
FIG. 8 is a bar graph showing the heat inactivation of subtilisin B24 compared to proteinase K.

The results indicated that subtilisin B24 was more heat labile than proteinase K (FIG. 8). More specifically, subtilisin B24 retained most of its activity at 40° C. for up to 30 minutes. This represents a typical digestion performed in molecular biology protocols, which are often done at 37° C. At 50° C., most of the subtilisin B24 activity was lost by 30 minutes. At 60° C. or 70° C. an incubation of 10 minutes or more eliminated all detectable protease activity from subtilisin B24. In contrast, proteinase K, the most commonly used laboratory protease, remains fully active after 30 minutes at 60° C., and still retains some activity after 30 minutes when incubated at 70° C. Thus, there are widely differing heat stability properties between subtilisin B24 and proteinase K. The instability of subtilisin B24 allows one to rapidly eliminate its protease activity at relatively moderate temperatures.

Subtilisin B24 Inactivation of Heat Stable Restriction Enzymes Pvu I and Pvu II

Figure 9:
FIG. 9 is a gel showing subtilisin B24 inactivation of heat stable restriction enzymes Pvu I and Pvu II. Lane 1: DNA Ladder; Lane 2: PvuI treated with B24, then lambda DNA added; Lane 3: PvuI treated with heat inactivated B24, then lambda DNA added; Lane 4: PvuII treated with B24, then lambda DNA added; Lane 5: PvuII treated with heat inactivated B24, then lambda DNA added; Lane 6: B24 with lambda DNA.

The restriction enzymes, Pvu I and Pvu II, are thermostable and are thus resistant to temperature inactivation, typically done at 65° C. or 80° C. The ability of subtilisin B24 to inactivate these enzymes was tested (FIG. 9). Briefly, the final reaction volume of the tests was 30 µl in 1×NEB 3.1 buffer (New England Biolabs, "NEB"). For lanes 2 and 4, 50 units of restriction enzymes Pvu I (NEB) and Pvu II (NEB) were incubated at 37° C. in the presence of 100 µg of subtilisin B24 for 1 hour. After this 1 hour treatment, subtilisin B24 was inactivated at 60° C. for 10 minutes. Then 2.5 µg of lambda DNA was added, and the tubes were incubated at 37° C. for another hour. For lanes 3 and 5, 100 µg of subtilisin B24 was heat inactivated at 60° C. for 10 minutes, then 50 units of restriction enzyme and 2.5 µg of DNA was added and incubated at 37° C. for an hour. Lastly, for lane 6, 100 µg of subtilisin B24 and 2.5 µg of DNA was incubated at 37° C. for 1 hour. 20 µL of each reaction was mixed with 5 µL of 6× loading dye and the full 25 µL was loaded onto a 1.5% agarose gel containing 2 µl of Gel Red™ (Biotium). Electrophoresis was carried out at 45V for 8 hours and then visualized using UV light. The results indicated that the subtilisin B24 variant digests and inactivates heat stable restrictions enzymes. More specifically, lanes 3 and 5 containing lamba DNA shows cutting of the lambda DNA as compared to the lambda DNA control containing no restriction enzyme in lane 6. Lanes 2 and 4 which contained restriction enzyme incubated with B24 (not heat treated) showed no lambda DNA digestion, which demonstrates that B24 inactivates heat-stable restriction enzymes Pvu I and Pvu II.

Figure 10:
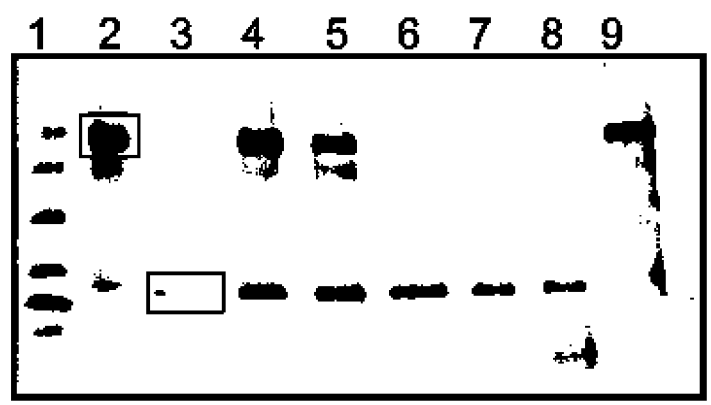
FIG. 10 is a gel showing subtilisin B24 inactivation of heat stable restriction enzyme Pvu II at different time points. 10 µg of subtilisin B24 was mixed with 100 units of Pvu II (NEB) and incubated from 0 (lane 4), 10 (lane 5), 15 (lane 6), 20 (lane 7) or 30 minutes (lane 8) at 37° C. Control lanes show just B24 (lane 3) or just Pvu II (lane 2). Inactivation of B24 at 60° C. for 20 minute prior to adding it to Pvu II led to no digestion of Pvu II (lane 9)

To visualize the digestion of Pvu II (FIG. 10), 10 µg of subtilisin B24 was mixed with 100 units of Pvu II (NEB) and incubated from 0 (lane 4), 10 (lane 5), 15 (lane 6), 20 (lane 7) or 30 minutes (lane 8) at 37° C. Control lanes show just B24 (lane 3) or just Pvu II (lane 2). Inactivation of B24 at 60° C. for 20 minute prior to adding it to Pvu II led to no digestion of Pvu II (lane 9).

Activity of Subtilisin B24 in the Presence of Detergents

Digestion of catalase and RNaseA (Bio Basic) with 10 µg of subtilisin B24 in the presence of varying concentrations of the detergents SDS, Triton X-100, and CTAB was determined. For each reaction condition, 10 µg of lyophilized catalase or RNase A and protease B24 were dissolved in 25 µL aliquots of 10 mM Tris-HCl, pH 8.0 containing the detergent. The 2×CTAB Buffer was 100 mM Tris-HCl, pH 8.0; 1.4M NaCl; 20 mM EDTA; 2% CTAB; 2% polyvinylpyrrolidone; 0.2% β-mercaptoethanol. The reactions were incubated at 37° C. for 1 hour. As a negative control, catalase and RNase A were incubated at 37° C. for 1 hour without subtilisin B24 in the presence of 1% detergent. After the incubation, 4×SDS loading dye was added to each sample and were incubated at 70° C. for 10 minutes, and then 20 µl was loaded onto a 12% SDS-PAGE gel. The gel was run at a constant current of 24 amps for 1 hour. The gel was Coomassie stained overnight.

Figure 11A:
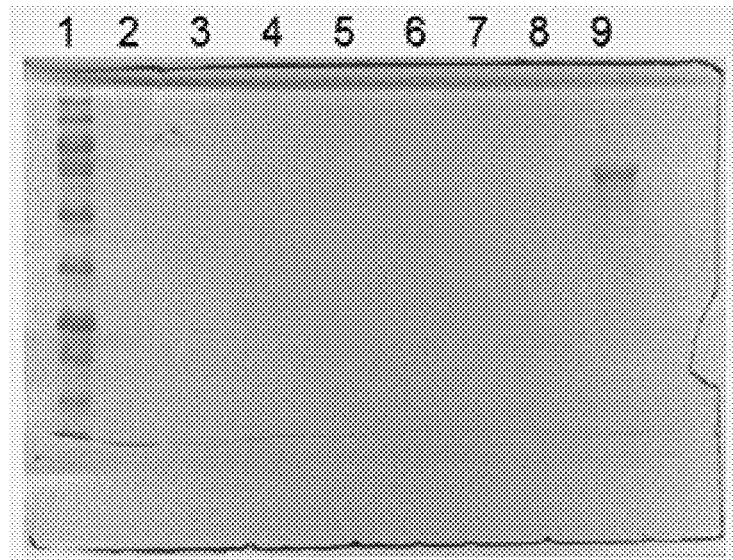
FIG. 11A is a gel showing digestion of catalase with subtilisin B24 in the presence of SDS. Lane 1: Molecular weight ladder; Lane 2: Catalase+B24; Lane 3: Catalase+B24+0.2% SDS; Lane 4: Catalase+B24+0.4% SDS; Lane 5: Catalase+B24+0.8% SDS; Lane 6: Catalase+B24+1.0% SDS; Lane 7: Catalase+B24+1.5% SDS; Lane 8: Catalase+B24+2.0% SDS; Lane 9: Catalase+1.0% SDS.
Figure 11B:
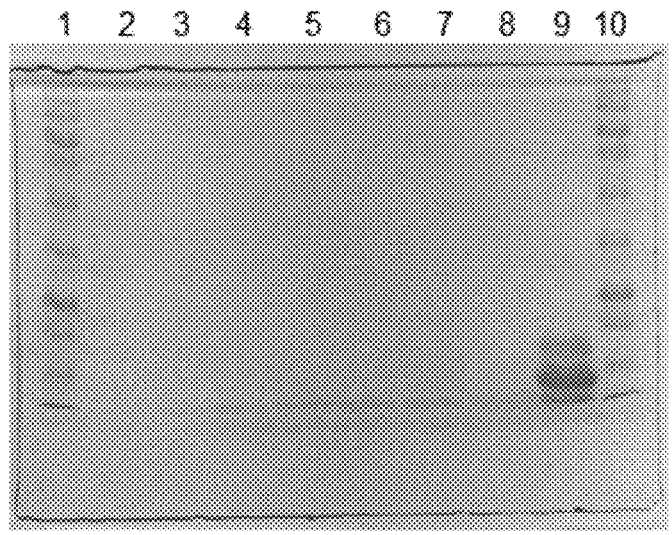
FIG. 11B is a gel showing digestion of RNase A with Subtilisin B24 in the presence of SDS. Lane 1: Molecular weight ladder; Lane 2: RNase A+B24; Lane 3: RNase A+B24+0.2% SDS; Lane 4: RNase A+B24+0.4% SDS; Lane 5: RNase A+B24+0.8% SDS; Lane 6: RNase A+B24+1.0% SDS; Lane 7: RNase A+B24+1.5% SDS; Lane 8: RNase A+B24+2.0% SDS; Lane 9: RNase A+1.0% SDS.
Figure 11C:
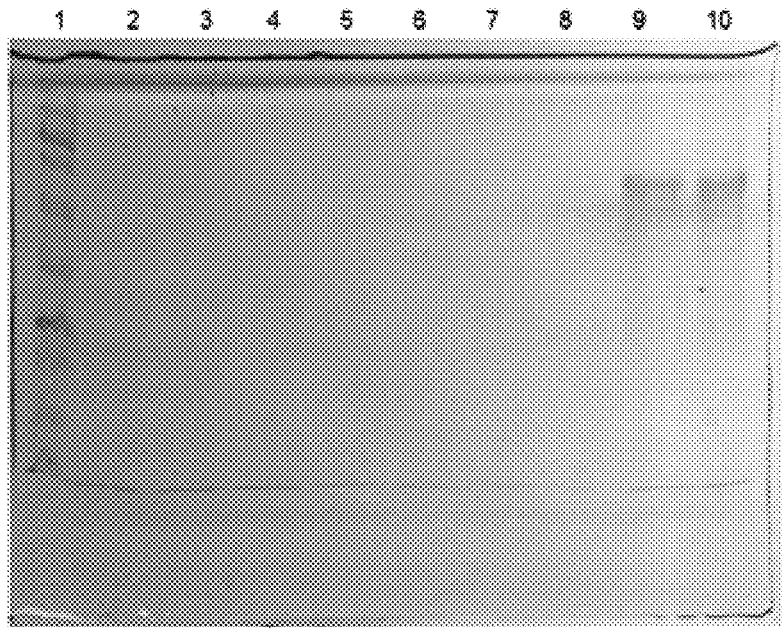
FIG. 11C is a gel showing digestion of catalase with subtilisin B24 in the presence of Triton X-100. Lane 1: Molecular weight ladder; Lane 2: Catalase+B24; Lane 3: Catalase+B24+0.2% Triton X-100; Lane 4: Catalase+B24+0.4% Triton X-100; Lane 5: Catalase+B24+0.8% Triton X-100; Lane 6: Catalase+B24+1.0% Triton X-100; Lane 7: Catalase+B24+1.5% Triton X-100; Lane 8: Catalase+B24+2.0% Triton X-100; Lane 9: Catalase+1.0% Triton X-100+Heat inactivated B24; Lane 10: Catalase.
Figure 11D:
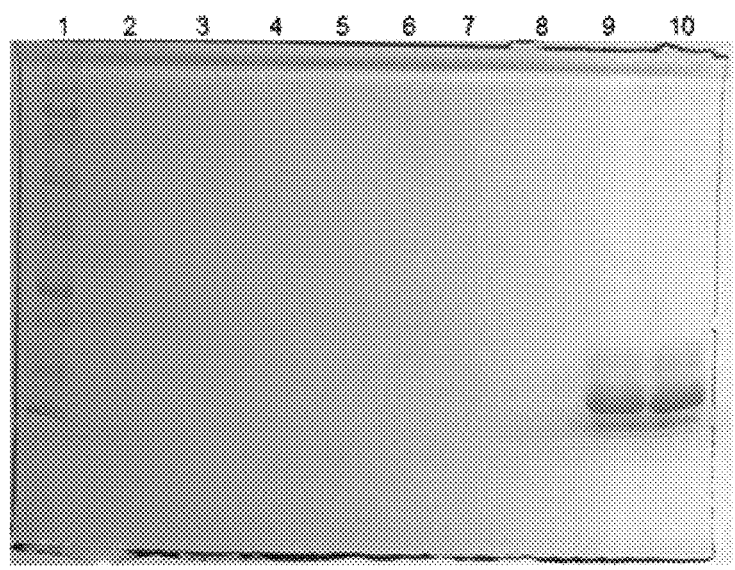
FIG. 11D is a gel showing digestion of RNase A with Subtilisin B24 in the presence of Triton X-100. Lane 1: Molecular weight ladder; Lane 2: RNase A+B24; Lane 3: RNase A+B24+0.2% Triton X-100; Lane 4: RNase A+B24+0.4% Triton X-100; Lane 5: RNase A+B24+0.8% Triton X-100; Lane 6: RNase A+B24+1.0% Triton X-100; Lane 7: RNase A+B24+1.5% Triton X-100; Lane 8: RNase A+B24+2.0% Triton X-100; Lane 9: RNase A+1.0% Triton X-100; Lane 10: RNase A.
Figure 11E:
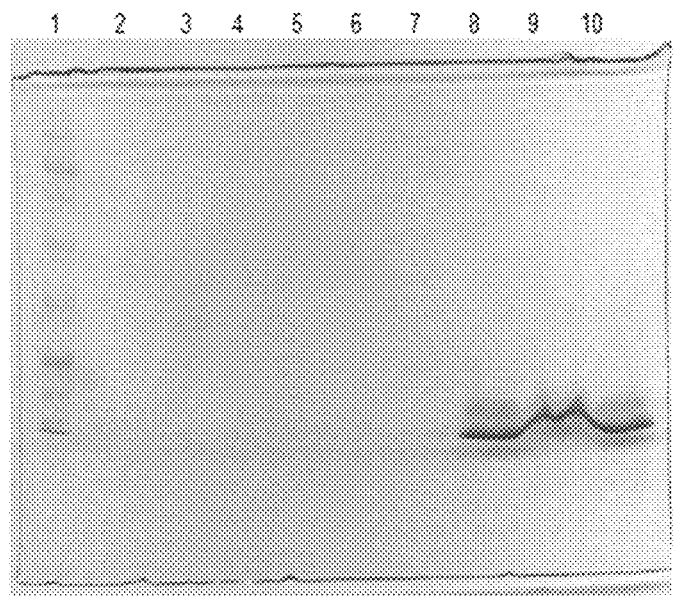
FIG. 11E is a gel showing digestion of RNase A with Subtilisin B24 in the presence of CTAB. Lane 1: Molecular weight ladder; Lane 2: RNase A+B24; Lane 3: RNase A+B24+0.1×CTAB Buffer; Lane 4: RNase A+B24+0.2× CTAB Buffer; Lane 5: RNase A+B24+0.5×CTAB Buffer; Lane 6: RNase A+B24+1×CTAB Buffer; Lane 7: RNase A+B24+2×CTAB Buffer; Lane 8: RNase A; Lane 9: RNase A+2×CTAB Buffer; Lane 10: RNase A+Heated inactivated B24.

The results indicated that the subtilisin B24 variant can digest catalase (FIG. 11A) and RNAase (FIG. 11B) up to at least a 2.0% SDS concentration; catalase (FIG. 11C) and RNAase (FIG. 11D) up to at least a 2.0% Triton X-100 concentration; and RNAase (FIG. 11E) up to at least a 2% CTAB concentration.

Heat Treatment of Subtilisin B24 and Proteinase K

Figure 12A:
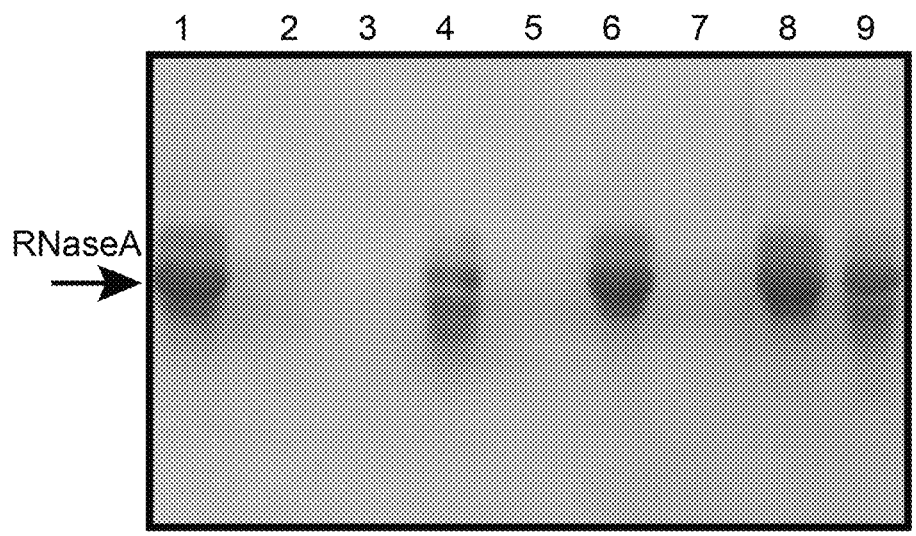
FIG. 12A is a gel showing the effect of heat treatment of subtilisin B24 and proteinase K on degradation of RNaseA; Lane 1: RNaseA; Lane 2: RNase A+B24; Lane 3: RNaseA+Proteinase K; Lane 4: RNaseA+Heat treated B24 (50° C. for 30 minutes); Lane 5: RNaseA+Heat treated proteinase K (50° C. for 30 minutes); Lane 6: RNaseA+Heat treated B24 (70° C. for 15 minutes); Lane 7: RNaseA+Heat treated proteinase K (70° C. for 15 minutes); Lane 8: RNaseA+Heat treated B24 (95° C. for 10 minutes); Lane 9: RNaseA+Heat treated proteinase K (95° C. for 10 minutes)
Figure 12B:
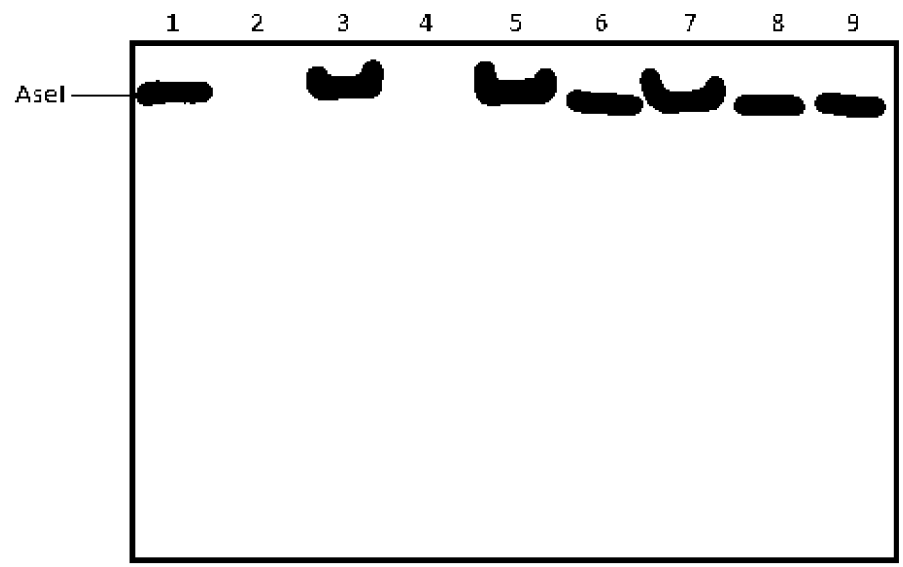
FIG. 12B is a gel showing the effect of heat treatment of subtilisin B24 and of proteinase K on degradation of the restriction enzyme Ase I; Lane 1: AseI; Lane 2: AseI+B24; Lane 3: AseI+Proteinase K; Lane 4: AseI+Heat treated B24 (50° C. for 30 minutes); Lane 5: AseI+Heat treated proteinase K (50° C. for 30 minutes); Lane 6: AseI+Heat treated B24 (70° C. for 15 minutes); Lane 7: AseI+Heat treated proteinase K (70° C. for 15 minutes); Lane 8: AseI+Heat treated B24 (95° C. for 10 minutes); Lane 9: AseI+Heat treated proteinase K (95° C. for 10 minutes)

The subtilisin B24 variant and proteinase K (Bio Basic) were subjected to various exposure to heat. After the heat treatment, or mock treatment at room temperature, 5 µg of the subtilisin B24 variant or proteinase K (Biobasic) were mixed with 10 µg of RNaseA (Bio Basic, FIG. 12A) or the restriction enzyme Ase I (NEB, FIG. 12B) in a total of 20 µL of 10 mM Tris-HCl, pH 8.0, and incubated for 1 hour at 37° C. After the incubation, 4×SDS loading dye was added to each sample and were incubated at 70° C. for 10 minutes, and then 20 µL was loaded onto a 12% SDS-PAGE gel. The gel was run at a constant current of 24 amps for 1 hour. The gel was Coomassie stained overnight.

The results indicated that while both the subtilisin B24 variant and proteinase K can degrade RNaseA, the degradation activity of the subtilisin B24 variant is significantly reduced at 50° C. and eliminated at 70° C. in 15 minutes. By contrast, proteinase K activity is not eliminated at 70° C. for 15 min and the enzyme appears to retain some activity at 95° for 10 min.

The results also indicated that subtilisin B24 variant can digest Ase I in one hour at 37° C. while Proteinase K cannot.

Temperature Inactivation Subtilisin B24 and Variants of Subtilisin B24

Figure 13:
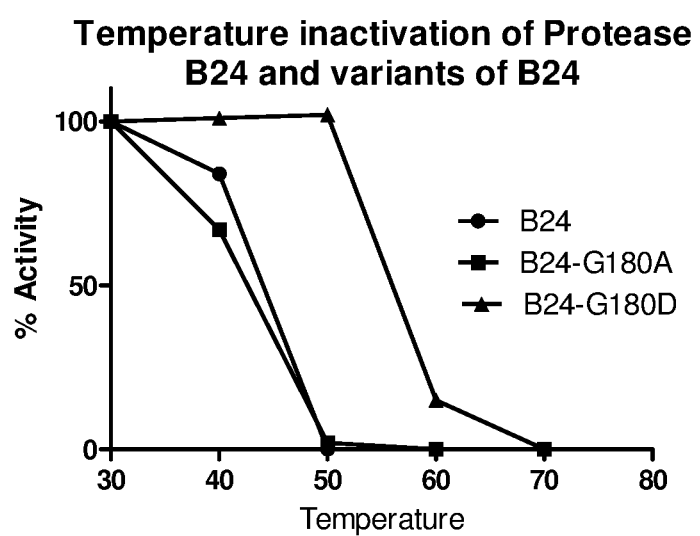
FIG. 13 is a graph showing the activity of subtilisin B24 and variants of subtilisin B24.

Amino acid residue 180 was changed to either an alanine (A) or an aspartic acid (D) residue, which is the amino acid residue found in the wild type parent subtilisin, in the context of the subtilisin B24 variant. B24G, B24-G180A, and B24-G180D were incubated between 30° C.-70° C. for 1 hour, as described herein. Protease activity was detected using a Pierce fluorescent protease assay kit and the percent activity was calculated using 30° C. activity as 100%. The G180A variant change exhibited a similar effect on protease thermostability as the subtilisin B24 D180D variant (FIG. 13). By contrast, the G180D variant change increased the stability considerably (FIG. 13).

All citations are hereby incorporated by reference.

As used herein the singular forms "a", "and", and "the" include plural referents unless the context clearly dictates otherwise. For example, "a variant" refers to one or more of such variants, "a cell" refers to a plurality of cells, while "the enzyme" includes a particular enzyme as well as other family member equivalents thereof as known to those skilled in the art.

The present invention has been described with regard to one or more embodiments. However, it will be apparent to persons skilled in the art that a number of variations and modifications can be made without departing from the scope of the invention as defined in the claims.

What is claimed is:

1. A variant subtilisin Carlsberg polypeptide, or a processed fragment thereof, the polypeptide comprising a mutation at one or more of amino acid positions K88, D180, N181, N265, L339 or Q379, wherein the amino acid position corresponds to the numbering set forth in SEQ ID NO:2, or combinations thereof, and wherein the polypeptide is heat labile.

2. The variant subtilisin Carlsberg polypeptide of claim 1 comprising a mutation at amino acid positions D180, L339 and Q379; L339 and Q379; D180 and L339; or D180 and Q379.

3. The variant subtilisin Carlsberg polypeptide of claim 1 wherein the mutation at K88 is K88N, the mutation at D180 is D180G or D180A, the mutation at N181 is N181Y, the mutation at N265 is N265S, the mutation at L339 is L339M, or the mutation at Q379 is Q379P.

4. The variant subtilisin Carlsberg polypeptide of claim 1 comprising D180G, L339M, and Q379P substitutions (SEQ ID NO: 9, SEQ ID NO: 10, SEQ ID NO: 23, SEQ ID NO: 24, SEQ ID NO: 25 or SEQ ID NO: 26), L339M and Q379P substitutions (SEQ ID NO: 11 or SEQ ID NO: 12), D180A, L339M, and Q379P substitutions (SEQ ID NO: 13 or SEQ ID NO: 14), wherein the amino acid position number corresponds to the numbering set forth in SEQ ID NO: 2.

5. The variant subtilisin Carlsberg polypeptide of claim 1 comprising the sequence set forth in SEQ ID NO: 27 or 28, the polypeptide further comprising a mutation at amino acid positions: D180; L339; Q379; D180 and L339; D180 and Q379; L339 and Q379; or D180, L339 and Q379, wherein the amino acid position number corresponds to the numbering set forth in SEQ ID NO: 2.

6. A composition comprising the polypeptide of claim 1 and a carrier.

7. The composition of claim 6 wherein the composition is a detergent composition.

8. A nucleic acid molecule encoding the variant subtilisin Carlsberg polypeptide of claim 1.

9. An expression vector comprising the nucleic acid molecule of claim 8.

10. A host cell comprising the expression vector of claim 9.

11. The host cell of claim 10 wherein the host cell is a *Bacillus subtilis*.

12. A nucleic acid molecule encoding the variant subtilisin Carlsberg polypeptide of claim 4.

13. A nucleic acid molecule comprising the sequence set forth in any one of SEQ ID NOs: 3 to 8 or a fragment thereof, wherein the nucleic acid sequence encodes a polypeptide comprising D180G, L339M, and Q379P substitutions (SEQ ID NO: 3 or SEQ ID NO: 4), L339M and Q379P substitutions (SEQ ID NO: 5 or SEQ ID NO: 6), D180A, L339M, and Q379P substitutions (SEQ ID NO: 7 or SEQ ID NO: 8), wherein the amino acid position number corresponds to the numbering set forth in SEQ ID NO: 2.

14. A method of removing a target polypeptide from a sample comprising:
   i) providing a sample comprising the target polypeptide; and
   ii) contacting the variant subtilisin Carlsberg polypeptide of claim 1 with the target polypeptide to remove the target polypeptide.

15. The method of claim 14 further comprising inactivating the variant subtilisin Carlsberg polypeptide.

16. The method of claim 15 wherein the inactivating is performed by increasing the temperature to 50° C.

17. The method of claim 14 wherein the target polypeptide is an enzyme.

18. The method of claim 17 wherein the enzyme is a heat resistant enzyme, a nuclease, a DNA modifying enzyme, or a restriction enzyme.

19. The method of claim 14 wherein the sample is a preparation of plasmid DNA, a preparation of chromosomal DNA, a preparation of mitochondrial DNA, a preparation of RNA, a forensic sample, a clinical sample, or a diagnostic sample.

20. The method of claim 14 wherein the target polypeptide is a contaminant.

\* \* \* \* \*

SEQUENCE LISTING

```
<160> NUMBER OF SEQ ID NOS: 28

<210> SEQ ID NO 1
<211> LENGTH: 1244
<212> TYPE: DNA
<213> ORGANISM: Artificial Sequence
<220> FEATURE:
<223> OTHER INFORMATION: variant subtilisin Carlsberg sequence

<400> SEQUENCE: 1
acagcccaag ctttctagag tccatatagg ataggagatt gatgtatgat gaggaaaaag    60
```

-continued

```
agttttggc ttgggatgct gacggccttc atgctcgtgt tcacgatggc attcagcgat    120
tccgcttctg ctgctcaacc ggcgaaaaat gttgaaaagg attatattgt cggatttaag    180
tcaggagtga aaaccgcatc tgtcaaaaag gacatcatca agagagcgg cggaaaagtg    240
gacaagcagt ttagaatcat caacgcggca aaagcgaagc tagacaaaga agcgcttaag    300
gaagtcaaaa atgatccgga tgtcgcttat gtggaagagg atcatgtggc ccatgccttg    360
gcgcaaaccg ttccttacgg cattcctctc attaaagcgg acaaagtgca ggctcaaggc    420
tttaagggag cgaatgtaaa agtagccgtc ctggatacag gaatccaagc ttctcatccg    480
gacttgaacg tagtcggcgg agcaagcttt gtggctggcg aagcttataa caccgacggc    540
aacggacacg gcacacatgt tgccggtaca gtagctgcgc ttgacaatac aacgggtgta    600
ttaggcgttg cgccaagcgt atccttgtac gcggttaaag tactgaattc aagcggaagc    660
ggatcataca gcggcattgt aagcggaatc gagtgggcga caacaaacgg catggatgtt    720
atcaatatga gccttggggg agcatcaggc tcgacagcga tgaaacaggc agtcgacaat    780
gcatatgcaa aaggggttgt cgttgtagct gcagcaggga acagcggatc ttcaggaaac    840
acgaatacaa ttggctatcc tgcgaaatac gattctgtca tcgctgttgg tgcggtagac    900
tctaacagca acagagcttc atttttccagt gtgggagcag agcttgaagt catggctcct    960
ggcgcaggcg tatacagcac ttacccaacg aacacttatg caacattgaa cggaacgtca    1020
atggcttctc ctcatgtagc gggagcagca gctttgatct tgtcaaaaca tccgaacctt    1080
tcagcttcac aagtccgcaa ccgtctctcc agcacggcga cttatttggg aagctccttc    1140
tactatggga aaggtctgat caatgtcgaa gctgccgctc aacatcacca ccatcaccat    1200
taatgagatc aacagtttgg gcagttgacg gatccgggga attc                     1244
```

<210> SEQ ID NO 2  
<211> LENGTH: 379  
<212> TYPE: PRT  
<213> ORGANISM: Bacillus licheniformis

<400> SEQUENCE: 2

```
Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
        115                 120                 125

Ala Asn Val Lys Val Ala Val Leu Asp Thr Gly Ile Gln Ala Ser His
    130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
```

165                 170                 175
Ala Ala Leu Asp Asn Thr Thr Gly Val Leu Gly Val Ala Pro Ser Val
                    180                 185                 190

Ser Leu Tyr Ala Val Lys Val Leu Asn Ser Ser Gly Ser Gly Ser Tyr
                195                 200                 205

Ser Gly Ile Val Ser Gly Ile Glu Trp Ala Thr Thr Asn Gly Met Asp
            210                 215                 220

Val Ile Asn Met Ser Leu Gly Gly Ala Ser Gly Ser Thr Ala Met Lys
225                 230                 235                 240

Gln Ala Val Asp Asn Ala Tyr Ala Lys Gly Val Val Val Ala Ala
                    245                 250                 255

Ala Gly Asn Ser Gly Ser Ser Gly Asn Thr Asn Thr Ile Gly Tyr Pro
                260                 265                 270

Ala Lys Tyr Asp Ser Val Ile Ala Val Gly Ala Val Asp Ser Asn Ser
            275                 280                 285

Asn Arg Ala Ser Phe Ser Ser Val Gly Ala Glu Leu Glu Val Met Ala
290                 295                 300

Pro Gly Ala Gly Val Tyr Ser Thr Tyr Pro Thr Asn Thr Tyr Ala Thr
305                 310                 315                 320

Leu Asn Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Asn
                340                 345                 350

Arg Leu Ser Ser Thr Ala Thr Tyr Leu Gly Ser Ser Phe Tyr Tyr Gly
                355                 360                 365

Lys Gly Leu Ile Asn Val Glu Ala Ala Ala Gln
            370                 375

<210> SEQ ID NO 3
<211> LENGTH: 1158
<212> TYPE: DNA
<213> ORGANISM: Artificial Sequence
<220> FEATURE:
<223> OTHER INFORMATION: variant subtilisin Carlsberg sequence

<400> SEQUENCE: 3
atgatgagga aaaagagttt ttggcttggg atgctgacgg ccttcatgct cgtgttcacg      60
atggcattca gcgattccgc ttctgctgct caaccggcga aaatgttga aaggattat      120
attgtcggat ttaagtcagg agtgaaaacc gcatctgtca aaaggacat catcaaagag      180
agcggcggaa aagtggacaa gcagtttaga atcatcaacg cggcaaaagc gaagctagac      240
aaagaagcgc ttaaggaagt caaaaatgat ccggatgtcg cttatgtgga gaggatcat      300
gtggcccatg ccttggcgca aaccgttcct tacggcattc ctctcattaa agcggacaaa      360
gtgcaggctc aaggctttaa gggagcgaat gtaaaagtag ccgtcctgga tacaggaatc      420
caagcttctc atccggactt gaacgtagtc ggcggagcaa gctttgtggc tggcgaggct      480
tataacaccg acggcaacgg acacggcaca catgttgccg gtacagtagc tgcgcttggc      540
aatacaacgg gtgtattagg cgttgcgcca agcgtatcct tgtacgcggt taaagtactg      600
aattcaagcg gaagcggatc atacagcggc attgtaagcg gaatcgagtg ggcgacaaca      660
aacggcatgg atgttatcaa tatgagcctt ggggagcat caggctcgac agcgatgaaa      720
caggcagtcg acaatgcata tgcaaaaggg gttgtcgttg tagctgcagc agggaacagc      780
ggatcttcag gaaacacgaa tacaattggc tatcctgcga aatacgattc tgtcatcgct      840

```
gttggtgcgg tagactctaa cagcaacaga gcttcatttt ccagtgtggg agcagagctt     900
gaagtcatgg ctcctggcgc aggcgtatac agcacttacc caacgaacac ttatgcaaca     960
ttgaacggaa cgtcaatggc ttctcctcat gtagcgggag cagcggcttt gatcatgtca    1020
aaacatccga acctttcagc ttcacaagtc cgcaaccgtc tctccagcac ggcgacttat    1080
ttgggaagct ccttctacta tgggaaaggt ctgatcaatg tcgaagctgc cgctccacat    1140
caccaccatc accattaa                                                  1158
```

<210> SEQ ID NO 4
<211> LENGTH: 1140
<212> TYPE: DNA
<213> ORGANISM: Artificial Sequence
<220> FEATURE:
<223> OTHER INFORMATION: variant subtilisin Carlsberg sequence

<400> SEQUENCE: 4

```
atgatgagga aaagagtttt ttggcttggg atgctgacgg ccttcatgct cgtgttcacg      60
atggcattca gcgattccgc ttctgctgct caaccggcga aaaatgttga aaaggattat     120
attgtcggat ttaagtcagg agtgaaaacc gcatctgtca aaaggacat catcaaagag      180 agcggcggaa aagtggacaa gcagtttaga atcatcaacg cggcaaaagc gaagctagac     240
aaagaagcgc ttaaggaagt caaaaatgat ccggatgtcg cttatgtgga agaggatcat     300
gtggcccatg ccttggcgca aaccgttcct tacggcattc ctctcattaa agcggacaaa     360
gtgcaggctc aaggctttaa gggagcgaat gtaaaagtag ccgtcctgga tacaggaatc     420
caagcttctc atccggactt gaacgtagtc ggcggagcaa gctttgtggc tggcgaggct     480
tataacaccg acggcaacgg acacggcaca catgttgccg gtacagtagc tgcgcttggc     540
aatacaacgg gtgtattagg cgttgcgcca agcgtatcct tgtacgcggt taaagtactg     600
aattcaagcg gaagcggatc atacagcggc attgtaagcg gaatcgagtg ggcgacaaca     660
aacggcatga tgttatcaa tatgagcctt gggggagcat caggctcgac agcgatgaaa     720
caggcagtcg acaatgcata tgcaaaaggg gttgtcgttg tagctgcagc agggaacagc     780
ggatcttcag gaaacacgaa tacaattggc tatcctgcga aatacgattc tgtcatcgct     840
gttggtgcgg tagactctaa cagcaacaga gcttcatttt ccagtgtggg agcagagctt     900
gaagtcatgg ctcctggcgc aggcgtatac agcacttacc caacgaacac ttatgcaaca     960
ttgaacggaa cgtcaatggc ttctcctcat gtagcgggag cagcggcttt gatcatgtca    1020
aaacatccga acctttcagc ttcacaagtc cgcaaccgtc tctccagcac ggcgacttat    1080
ttgggaagct ccttctacta tgggaaaggt ctgatcaatg tcgaagctgc cgctccataa    1140
```

<210> SEQ ID NO 5
<211> LENGTH: 1158
<212> TYPE: DNA
<213> ORGANISM: Artificial Sequence
<220> FEATURE:
<223> OTHER INFORMATION: variant subtilisin Carlsberg sequence

<400> SEQUENCE: 5

```
atgatgagga aaagagtttt ttggcttggg atgctgacgg ccttcatgct cgtgttcacg      60
atggcattca gcgattccgc ttctgctgct caaccggcga aaaatgttga aaaggattat     120
attgtcggat ttaagtcagg agtgaaaacc gcatctgtca aaaggacat catcaaagag      180 agcggcggaa aagtggacaa gcagtttaga atcatcaacg cggcaaaagc gaagctagac     240
aaagaagcgc ttaaggaagt caaaaatgat ccggatgtcg cttatgtgga agaggatcat     300
```

```
gtggcccatg ccttggcgca aaccgttcct tacggcattc ctctcattaa agcggacaaa      360
gtgcaggctc aaggctttaa gggagcgaat gtaaaagtag ccgtcctgga tacaggaatc      420
caagcttctc atccggactt gaacgtagtc ggcggagcaa gctttgtggc tggcgaggct      480
tataacaccg acggcaacgg acacggcaca catgttgccg gtacagtagc tgcgcttgat      540
aatacaacgg gtgtattagg cgttgcgcca agcgtatcct tgtacgcggt taaagtactg      600
aattcaagcg gaagcggatc atacagcggc attgtaagcg gaatcgagtg ggcgacaaca      660
aacggcatgg atgttatcaa tatgagcctt gggggagcat caggctcgac agcgatgaaa      720
caggcagtcg acaatgcata tgcaaaaggg gttgtcgttg tagctgcagc agggaacagc      780
ggatcttcag gaaacacgaa tacaattggc tatcctgcga aatacgattc tgtcatcgct      840
gttggtgcgg tagactctaa cagcaacaga gcttcatttt ccagtgtggg agcagagctt      900
gaagtcatgg ctcctggcgc aggcgtatac agcacttacc caacgaacac ttatgcaaca      960
ttgaacggaa cgtcaatggc ttctcctcat gtagcgggag cagcggcttt gatcatgtca     1020
aaacatccga acctttcagc ttcacaagtc cgcaaccgtc tctccagcac ggcgacttat     1080
ttgggaagct ccttctacta tgggaaaggt ctgatcaatg tcgaagctgc cgctccacat     1140
caccaccatc accattaa                                                   1158

<210> SEQ ID NO 6
<211> LENGTH: 1140
<212> TYPE: DNA
<213> ORGANISM: Artificial Sequence
<220> FEATURE:
<223> OTHER INFORMATION: variant subtilisin Carlsberg sequence

<400> SEQUENCE: 6
atgatgagga aaagagtttt ttggcttggg atgctgacgg ccttcatgct cgtgttcacg       60
atggcattca gcgattccgc ttctgctgct caaccggcga aaaatgttga aaaggattat      120
attgtcggat ttaagtcagg agtgaaaacc gcatctgtca aaaaggacat catcaaagag      180
agcggcggaa aagtggacaa gcagtttaga atcatcaacg cggcaaaagc gaagctagac      240
aaagaagcgc ttaaggaagt caaaaatgat ccggatgtcg cttatgtgga agaggatcat      300
gtggcccatg ccttggcgca aaccgttcct tacggcattc ctctcattaa agcggacaaa      360
gtgcaggctc aaggctttaa gggagcgaat gtaaaagtag ccgtcctgga tacaggaatc      420
caagcttctc atccggactt gaacgtagtc ggcggagcaa gctttgtggc tggcgaggct      480
tataacaccg acggcaacgg acacggcaca catgttgccg gtacagtagc tgcgcttgat      540
aatacaacgg gtgtattagg cgttgcgcca agcgtatcct tgtacgcggt taaagtactg      600
aattcaagcg gaagcggatc atacagcggc attgtaagcg gaatcgagtg ggcgacaaca      660
aacggcatgg atgttatcaa tatgagcctt gggggagcat caggctcgac agcgatgaaa      720
caggcagtcg acaatgcata tgcaaaaggg gttgtcgttg tagctgcagc agggaacagc      780
ggatcttcag gaaacacgaa tacaattggc tatcctgcga aatacgattc tgtcatcgct      840
gttggtgcgg tagactctaa cagcaacaga gcttcatttt ccagtgtggg agcagagctt      900
gaagtcatgg ctcctggcgc aggcgtatac agcacttacc caacgaacac ttatgcaaca      960
ttgaacggaa cgtcaatggc ttctcctcat gtagcgggag cagcggcttt gatcatgtca     1020
aaacatccga acctttcagc ttcacaagtc cgcaaccgtc tctccagcac ggcgacttat     1080
ttgggaagct ccttctacta tgggaaaggt ctgatcaatg tcgaagctgc cgctccataa     1140
```

<210> SEQ ID NO 7
<211> LENGTH: 1158
<212> TYPE: DNA
<213> ORGANISM: Artificial Sequence
<220> FEATURE:
<223> OTHER INFORMATION: variant subtilisin Carlsberg sequence

<400> SEQUENCE: 7

```
atgatgagga aaaagagttt ttggcttggg atgctgacgg ccttcatgct cgtgttcacg      60
atggcattca gcgattccgc ttctgctgct caaccggcga aaaatgttga aaaggattat     120
attgtcggat ttaagtcagg agtgaaaacc gcatctgtca aaaaggacat catcaaagag     180
agcggcggaa aagtggacaa gcagtttaga atcatcaacg cggcaaaagc gaagctagac     240
aaagaagcgc ttaaggaagt caaaaatgat ccggatgtcg cttatgtgga agaggatcat     300
gtggcccatg ccttggcgca aaccgttcct tacggcattc ctctcattaa agcggacaaa     360
gtgcaggctc aaggctttaa gggagcgaat gtaaaagtag ccgtcctgga tacaggaatc     420
caagcttctc atccggactt gaacgtagtc ggcggagcaa gctttgtggc tggcgaggct     480
tataacaccg acggcaacgg acacggcaca catgttgccg gtacagtagc tgcgcttgca     540
aatacaacgg gtgtattagg cgttgcgcca agcgtatcct tgtacgcggt taaagtactg     600
aattcaagcg gaagcggatc atacagcggc attgtaagcg gaatcgagtg ggcgacaaca     660
aacggcatgg atgttatcaa tatgagcctt ggggagcat caggctcgac agcgatgaaa     720
caggcagtcg acaatgcata tgcaaaaggg gttgtcgttg tagctgcagc agggaacagc     780
ggatcttcag aaacacgaa tacaattggc tatcctgcga aatacgattc tgtcatcgct     840
gttggtgcgg tagactctaa cagcaacaga gcttcatttt ccagtgtggg agcagagctt     900
gaagtcatgg ctcctggcgc aggcgtatac agcacttacc caacgaacac ttatgcaaca     960
ttgaacggaa cgtcaatggc ttctcctcat gtagcgggag cagcggcttt gatcatgtca    1020
aaacatccga acctttcagc ttcacaagtc cgcaaccgtc tctccagcac ggcgacttat    1080
ttgggaagct ccttctacta tgggaaaggt ctgatcaatg tcgaagctgc cgctccacat    1140
caccaccatc accattaa                                                   1158
```

<210> SEQ ID NO 8
<211> LENGTH: 1140
<212> TYPE: DNA
<213> ORGANISM: Artificial Sequence
<220> FEATURE:
<223> OTHER INFORMATION: variant subtilisin Carlsberg sequence

<400> SEQUENCE: 8

```
atgatgagga aaaagagttt ttggcttggg atgctgacgg ccttcatgct cgtgttcacg      60
atggcattca gcgattccgc ttctgctgct caaccggcga aaaatgttga aaaggattat     120
attgtcggat ttaagtcagg agtgaaaacc gcatctgtca aaaaggacat catcaaagag     180
agcggcggaa aagtggacaa gcagtttaga atcatcaacg cggcaaaagc gaagctagac     240
aaagaagcgc ttaaggaagt caaaaatgat ccggatgtcg cttatgtgga agaggatcat     300
gtggcccatg ccttggcgca aaccgttcct tacggcattc ctctcattaa agcggacaaa     360
gtgcaggctc aaggctttaa gggagcgaat gtaaaagtag ccgtcctgga tacaggaatc     420
caagcttctc atccggactt gaacgtagtc ggcggagcaa gctttgtggc tggcgaggct     480
tataacaccg acggcaacgg acacggcaca catgttgccg gtacagtagc tgcgcttgca     540
aatacaacgg gtgtattagg cgttgcgcca agcgtatcct tgtacgcggt taaagtactg     600
```

```
aattcaagcg gaagcggatc atacagcggc attgtaagcg gaatcgagtg ggcgacaaca    660
aacggcatgg atgttatcaa tatgagcctt gggggagcat caggctcgac agcgatgaaa    720
caggcagtcg acaatgcata tgcaaaaggg gttgtcgttg tagctgcagc agggaacagc    780
ggatcttcag gaaacacgaa tacaattggc tatcctgcga aatacgattc tgtcatcgct    840
gttggtgcgg tagactctaa cagcaacaga gcttcatttt ccagtgtggg agcagagctt    900
gaagtcatgg ctcctggcgc aggcgtatac agcacttacc caacgaacac ttatgcaaca    960
ttgaacggaa cgtcaatggc ttctcctcat gtagcgggag cagcggcttt gatcatgtca   1020
aaacatccga acctttcagc ttcacaagtc cgcaaccgtc tctccagcac ggcgacttat   1080
ttgggaagct ccttctacta tgggaaaggt ctgatcaatg tcgaagctgc cgctccataa   1140
```

<210> SEQ ID NO 9
<211> LENGTH: 385
<212> TYPE: PRT
<213> ORGANISM: Artificial Sequence
<220> FEATURE:
<223> OTHER INFORMATION: variant subtilisin Carlsberg sequence

<400> SEQUENCE: 9

```
Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
        115                 120                 125

Ala Asn Val Lys Val Ala Val Leu Asp Thr Gly Ile Gln Ala Ser His
    130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Gly Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
        195                 200                 205

Ser Gly Ile Val Ser Gly Ile Glu Trp Ala Thr Thr Asn Gly Met Asp
    210                 215                 220

Val Ile Asn Met Ser Leu Gly Gly Ala Ser Gly Ser Thr Ala Met Lys
225                 230                 235                 240

Gln Ala Val Asp Asn Ala Tyr Ala Lys Gly Val Val Val Val Ala Ala
                245                 250                 255

Ala Gly Asn Ser Gly Ser Ser Gly Asn Thr Asn Thr Ile Gly Tyr Pro
            260                 265                 270
```

```
Ala Lys Tyr Asp Ser Val Ile Ala Val Gly Ala Val Asp Ser Asn Ser
            275                 280                 285

Asn Arg Ala Ser Phe Ser Ser Val Gly Ala Glu Leu Glu Val Met Ala
290                 295                 300

Pro Gly Ala Gly Val Tyr Ser Thr Tyr Pro Thr Asn Thr Tyr Ala Thr
305                 310                 315                 320

Leu Asn Gly Thr Ser Met Ala Ser Pro His Val Ala Gly Ala Ala Ala
                325                 330                 335

Leu Ile Met Ser Lys His Pro Asn Leu Ser Ala Ser Gln Val Arg Asn
                340                 345                 350

Arg Leu Ser Ser Thr Ala Thr Tyr Leu Gly Ser Ser Phe Tyr Tyr Gly
                355                 360                 365

Lys Gly Leu Ile Asn Val Glu Ala Ala Ala Pro His His His His His
        370                 375                 380

His
385

<210> SEQ ID NO 10
<211> LENGTH: 379
<212> TYPE: PRT
<213> ORGANISM: Artificial Sequence
<220> FEATURE:
<223> OTHER INFORMATION: variant subtilisin Carlsberg sequence

<400> SEQUENCE: 10

Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
                20                  25                  30

Ala Lys Asn Val Glu Lys Asp Tyr Ile Val Gly Phe Lys Ser Gly Val
                35                  40                  45

Lys Thr Ala Ser Val Lys Lys Asp Ile Ile Lys Glu Ser Gly Gly Lys
        50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
            115                 120                 125

Ala Asn Val Lys Val Ala Val Leu Asp Thr Gly Ile Gln Ala Ser His
130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Gly Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
            195                 200                 205

Ser Gly Ile Val Ser Gly Ile Glu Trp Ala Thr Thr Asn Gly Met Asp
        210                 215                 220

Val Ile Asn Met Ser Leu Gly Gly Ala Ser Gly Ser Thr Ala Met Lys
225                 230                 235                 240
```

```
Gln Ala Val Asp Asn Ala Tyr Ala Lys Gly Val Val Val Ala Ala
            245                 250                 255

Ala Gly Asn Ser Gly Ser Ser Gly Asn Thr Asn Thr Ile Gly Tyr Pro
            260                 265                 270

Ala Lys Tyr Asp Ser Val Ile Ala Val Gly Ala Val Asp Ser Asn Ser
            275                 280                 285

Asn Arg Ala Ser Phe Ser Ser Val Gly Ala Glu Leu Glu Val Met Ala
            290                 295                 300

Pro Gly Ala Gly Val Tyr Ser Thr Tyr Pro Thr Asn Thr Tyr Ala Thr
305                 310                 315                 320

Leu Asn Gly Thr Ser Met Ala Ser Pro His Val Ala Gly Ala Ala Ala
            325                 330                 335

Leu Ile Met Ser Lys His Pro Asn Leu Ser Ala Ser Gln Val Arg Asn
            340                 345                 350

Arg Leu Ser Ser Thr Ala Thr Tyr Leu Gly Ser Ser Phe Tyr Tyr Gly
            355                 360                 365

Lys Gly Leu Ile Asn Val Glu Ala Ala Pro
            370                 375
```

<210> SEQ ID NO 11
<211> LENGTH: 385
<212> TYPE: PRT
<213> ORGANISM: Artificial Sequence
<220> FEATURE:
<223> OTHER INFORMATION: variant subtilisin Carlsberg sequence

<400> SEQUENCE: 11

```
Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
            35                  40                  45

Lys Thr Ala Ser Val Lys Lys Asp Ile Ile Lys Glu Ser Gly Gly Lys
        50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
            115                 120                 125

Ala Asn Val Lys Val Ala Val Leu Asp Thr Gly Ile Gln Ala Ser His
        130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
            195                 200                 205

Ser Gly Ile Val Ser Gly Ile Glu Trp Ala Thr Thr Asn Gly Met Asp
        210                 215                 220
```

```
Val Ile Asn Met Ser Leu Gly Gly Ala Ser Gly Ser Thr Ala Met Lys
225                 230                 235                 240

Gln Ala Val Asp Asn Ala Tyr Ala Lys Gly Val Val Val Val Ala Ala
            245                 250                 255

Ala Gly Asn Ser Gly Ser Ser Gly Asn Thr Asn Thr Ile Gly Tyr Pro
        260                 265                 270

Ala Lys Tyr Asp Ser Val Ile Ala Val Gly Ala Val Asp Ser Asn Ser
    275                 280                 285

Asn Arg Ala Ser Phe Ser Ser Val Gly Ala Glu Leu Glu Val Met Ala
290                 295                 300

Pro Gly Ala Gly Val Tyr Ser Thr Tyr Pro Thr Asn Thr Tyr Ala Thr
305                 310                 315                 320

Leu Asn Gly Thr Ser Met Ala Ser Pro His Val Ala Gly Ala Ala Ala
            325                 330                 335

Leu Ile Met Ser Lys His Pro Asn Leu Ser Ala Ser Gln Val Arg Asn
        340                 345                 350

Arg Leu Ser Ser Thr Ala Thr Tyr Leu Gly Ser Ser Phe Tyr Tyr Gly
    355                 360                 365

Lys Gly Leu Ile Asn Val Glu Ala Ala Ala Pro His His His His His
370                 375                 380

His
385

<210> SEQ ID NO 12
<211> LENGTH: 379
<212> TYPE: PRT
<213> ORGANISM: Artificial Sequence
<220> FEATURE:
<223> OTHER INFORMATION: variant subtilisin Carlsberg sequence

<400> SEQUENCE: 12

Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
        115                 120                 125

Ala Asn Val Lys Val Ala Val Leu Asp Thr Gly Ile Gln Ala Ser His
    130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Asp Asn Thr Thr Gly Val Leu Gly Val Ala Pro Ser Val
            180                 185                 190
```

```
Ser Leu Tyr Ala Val Lys Val Leu Asn Ser Ser Gly Ser Gly Ser Tyr
            195                 200                 205

Ser Gly Ile Val Ser Gly Ile Glu Trp Ala Thr Thr Asn Gly Met Asp
        210                 215                 220

Val Ile Asn Met Ser Leu Gly Gly Ala Ser Gly Ser Thr Ala Met Lys
225                 230                 235                 240

Gln Ala Val Asp Asn Ala Tyr Ala Lys Gly Val Val Val Ala Ala
                245                 250                 255

Ala Gly Asn Ser Gly Ser Ser Gly Asn Thr Asn Thr Ile Gly Tyr Pro
            260                 265                 270

Ala Lys Tyr Asp Ser Val Ile Ala Val Gly Ala Val Asp Ser Asn Ser
            275                 280                 285

Asn Arg Ala Ser Phe Ser Ser Val Gly Ala Glu Leu Glu Val Met Ala
        290                 295                 300

Pro Gly Ala Gly Val Tyr Ser Thr Tyr Pro Thr Asn Thr Tyr Ala Thr
305                 310                 315                 320

Leu Asn Gly Thr Ser Met Ala Ser Pro His Val Ala Gly Ala Ala Ala
                325                 330                 335

Leu Ile Met Ser Lys His Pro Asn Leu Ser Ala Ser Gln Val Arg Asn
            340                 345                 350

Arg Leu Ser Ser Thr Ala Thr Tyr Leu Gly Ser Ser Phe Tyr Tyr Gly
        355                 360                 365

Lys Gly Leu Ile Asn Val Glu Ala Ala Pro
370                 375
```

<210> SEQ ID NO 13
<211> LENGTH: 385
<212> TYPE: PRT
<213> ORGANISM: Artificial Sequence
<220> FEATURE:
<223> OTHER INFORMATION: variant subtilisin Carlsberg sequence

<400> SEQUENCE: 13

```
Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
        115                 120                 125

Ala Asn Val Lys Val Ala Val Leu Asp Thr Gly Ile Gln Ala Ser His
    130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175
```

```
Ala Ala Leu Ala Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
        195                 200                 205

Ser Gly Ile Val Ser Gly Ile Glu Trp Ala Thr Thr Asn Gly Met Asp
210                 215                 220

Val Ile Asn Met Ser Leu Gly Gly Ala Ser Gly Ser Thr Ala Met Lys
225                 230                 235                 240

Gln Ala Val Asp Asn Ala Tyr Ala Lys Gly Val Val Val Ala Ala
            245                 250                 255

Ala Gly Asn Ser Gly Ser Ser Gly Asn Thr Asn Thr Ile Gly Tyr Pro
            260                 265                 270

Ala Lys Tyr Asp Ser Val Ile Ala Val Gly Ala Val Asp Ser Asn Ser
        275                 280                 285

Asn Arg Ala Ser Phe Ser Ser Val Gly Ala Glu Leu Glu Val Met Ala
            290                 295                 300

Pro Gly Ala Gly Val Tyr Ser Thr Tyr Pro Thr Asn Thr Tyr Ala Thr
305                 310                 315                 320

Leu Asn Gly Thr Ser Met Ala Ser Pro His Val Ala Gly Ala Ala Ala
                325                 330                 335

Leu Ile Met Ser Lys His Pro Asn Leu Ser Ala Ser Gln Val Arg Asn
            340                 345                 350

Arg Leu Ser Ser Thr Ala Thr Tyr Leu Gly Ser Ser Phe Tyr Tyr Gly
        355                 360                 365

Lys Gly Leu Ile Asn Val Glu Ala Ala Pro His His His His His
        370                 375                 380

His
385

<210> SEQ ID NO 14
<211> LENGTH: 379
<212> TYPE: PRT
<213> ORGANISM: Artificial Sequence
<220> FEATURE:
<223> OTHER INFORMATION: variant subtilisin Carlsberg sequence

<400> SEQUENCE: 14

Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp
65                  70                  75                  80

Lys Glu Ala Leu Lys Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
        115                 120                 125

Ala Asn Val Lys Val Ala Val Leu Asp Thr Gly Ile Gln Ala Ser His
    130                 135                 140
```

```
Pro Asp Leu Asn Val Val Gly Gly Ala Ser Phe Val Ala Gly Glu Ala
145                 150                 155                 160

Tyr Asn Thr Asp Gly Asn His Gly Thr His Val Ala Gly Thr Val
                165                 170                 175

Ala Ala Leu Ala Asn Thr Thr Gly Val Leu Gly Val Ala Pro Ser Val
            180                 185                 190

Ser Leu Tyr Ala Val Lys Val Leu Asn Ser Ser Gly Ser Gly Ser Tyr
        195                 200                 205

Ser Gly Ile Val Ser Gly Ile Glu Trp Ala Thr Thr Asn Gly Met Asp
    210                 215                 220

Val Ile Asn Met Ser Leu Gly Gly Ala Ser Gly Ser Thr Ala Met Lys
225                 230                 235                 240

Gln Ala Val Asp Asn Ala Tyr Ala Lys Gly Val Val Val Ala Ala
                245                 250                 255

Ala Gly Asn Ser Gly Ser Ser Gly Asn Thr Asn Thr Ile Gly Tyr Pro
            260                 265                 270

Ala Lys Tyr Asp Ser Val Ile Ala Val Gly Ala Val Asp Ser Asn Ser
        275                 280                 285

Asn Arg Ala Ser Phe Ser Ser Val Gly Ala Glu Leu Glu Val Met Ala
    290                 295                 300

Pro Gly Ala Gly Val Tyr Ser Thr Tyr Pro Thr Asn Thr Tyr Ala Thr
305                 310                 315                 320

Leu Asn Gly Thr Ser Met Ala Ser Pro His Val Ala Gly Ala Ala Ala
                325                 330                 335

Leu Ile Met Ser Lys His Pro Asn Leu Ser Ala Ser Gln Val Arg Asn
            340                 345                 350

Arg Leu Ser Ser Thr Ala Thr Tyr Leu Gly Ser Ser Phe Tyr Tyr Gly
        355                 360                 365

Lys Gly Leu Ile Asn Val Glu Ala Ala Ala Pro
    370                 375

<210> SEQ ID NO 15
<211> LENGTH: 1158
<212> TYPE: DNA
<213> ORGANISM: Artificial Sequence
<220> FEATURE:
<223> OTHER INFORMATION: variant subtilisin Carlsberg sequence

<400> SEQUENCE: 15
atgatgagga aaaagagttt ttggcttggg atgctgacgg ccttcatgct cgtgttcacg     60
atggcattca gcgattccgc ttctgctgct caaccggcga aaatgttga aaaggattat    120 attgtcggat ttaagtcagg agtgaaaacc gcatctgtca aaaaggacat catcaaagag    180
agcggcggaa agtggacaa gcagtttaga atcatcaacg cggcaaaagc gaagctagac    240
aaagaagcgc ttaaggaagt caacaatgat ccagatgtcg cttatgtgga agaggatcat    300
gtggcccatg ccttggcgca aaccgttcct tacggcattc ctctcattaa agcggacaaa    360
gtgcaggccc aaggctttaa gggagcgaat gtaaaagtag ccgtcctgga tacaggaatc    420
caagcttctc atccggactt gaacgtagtc ggcggagcaa gctttgtggc tggcgaagct    480
tataacaccg acggcaacgg acacggcaca catgttgccg gtacagtagc tgcgcttggc    540
tatacaacgg tgtattagg cgttgcgcca agcgtatcct tgtacgcggt taaagtactg    600
aattcaagcg ggagcggatc atacagcggc attgtaagcg gaatcgagtg gcgacaaca    660 aacggcatgg atgttatcaa tatgagcctt ggggagcat caggctcgac agcgatgaaa    720
```

```
caggcagtcg acaatgcata tgcaaaaggg gttgtcgttg tagctgcagc agggaacagc    780
ggatcttcag gaagcacgaa tacaattggc tatcctgcga aatacgattc tgtcatcgct    840
gttggtgcgg tagactctaa cagcaacaga gcttcatttt ccagtgtggg agcagagctt    900
gaagtcatgg cccctggcgc aggcgtatac agcacttacc caacgaacac ttatgcaaca    960
tttaacggaa cgtcaatggc ttctcctcat gtagcgggag cagcagcttt gatcttgtca   1020
aaacatccga acctttcagc ttcacaagtc cgcaaccgtc tctccagcac ggcgacttat   1080
ttgggaagct ccttctacta tgggaaaggt ctgatcaatg tcgaagctgc cgctcaacat   1140
caccaccatc accattaa                                                 1158
```

<210> SEQ ID NO 16
<211> LENGTH: 1140
<212> TYPE: DNA
<213> ORGANISM: Artificial Sequence
<220> FEATURE:
<223> OTHER INFORMATION: variant subtilisin Carlsberg sequence

<400> SEQUENCE: 16

```
atgatgagga aaagagtttt ttggcttggg atgctgacgg ccttcatgct cgtgttcacg     60
atggcattca gcgattccgc ttctgctgct caaccggcga aaatgttga aaaggattat    120 attgtcggat ttaagtcagg agtgaaaacc gcatctgtca aaaaggacat catcaaagag    180
agcggcggaa aagtggacaa gcagtttaga atcatcaacg cggcaaaagc gaagctagac    240
aaagaagcgc ttaaggaagt caacaatgat ccagatgtcg cttatgtgga agaggatcat    300
gtggcccatg ccttggcgca aaccgttcct tacggcattc ctctcattaa agcggacaaa    360
gtgcaggccc aaggctttaa gggagcgaat gtaaaagtag ccgtcctgga tacaggaatc    420
caagcttctc atccggactt gaacgtagtc ggcggagcaa gctttgtggc tggcgaagct    480
tataacaccg acggcaacgg acacggcaca catgttgccg gtacagtagc tgcgcttggc    540
tatacaacgg gtgtattagg cgttgcgcca agcgtatcct tgtacgcggt taaagtactg    600
aattcaagcg ggagcggatc atacagcggc attgtaagcg gaatcgagtg ggcgacaaca    660
aacggcatgg atgttatcaa tatgagcctt ggggagcat caggctcgac agcgatgaaa    720
caggcagtcg acaatgcata tgcaaaaggg gttgtcgttg tagctgcagc agggaacagc    780
ggatcttcag gaagcacgaa tacaattggc tatcctgcga aatacgattc tgtcatcgct    840
gttggtgcgg tagactctaa cagcaacaga gcttcatttt ccagtgtggg agcagagctt    900
gaagtcatgg cccctggcgc aggcgtatac agcacttacc caacgaacac ttatgcaaca    960
tttaacggaa cgtcaatggc ttctcctcat gtagcgggag cagcagcttt gatcttgtca   1020
aaacatccga acctttcagc ttcacaagtc cgcaaccgtc tctccagcac ggcgacttat   1080
ttgggaagct ccttctacta tgggaaaggt ctgatcaatg tcgaagctgc cgctcaataa   1140
```

<210> SEQ ID NO 17
<211> LENGTH: 385
<212> TYPE: PRT
<213> ORGANISM: Artificial Sequence
<220> FEATURE:
<223> OTHER INFORMATION: variant subtilisin Carlsberg sequence

<400> SEQUENCE: 17

```
Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
```

Ala Lys Asn Val Glu Lys Asp Tyr Ile Val Gly Phe Lys Ser Gly Val
     20                  25                  30
Lys Thr Ala Ser Val Lys Lys Asp Ile Ile Lys Glu Ser Gly Gly Lys
 35                  40                  45
Val Asp Lys Gln Phe Arg Ile Ile Asn Ala Ala Lys Ala Lys Leu Asp
 50                  55                  60
Lys Glu Ala Leu Lys Glu Val Asn Asn Asp Pro Asp Val Ala Tyr Val
 65                  70                  75                  80
Glu Glu Asp His Val Ala His Ala Leu Ala Gln Thr Val Pro Tyr Gly
             85                  90                  95
Ile Pro Leu Ile Lys Ala Asp Lys Val Gln Ala Gln Gly Phe Lys Gly
            100                 105                 110
Ala Asn Val Lys Val Ala Val Leu Asp Thr Gly Ile Gln Ala Ser His
        115                 120                 125
Pro Asp Leu Asn Val Val Gly Gly Ala Ser Phe Val Ala Gly Glu Ala
    130                 135                 140
Tyr Asn Thr Asp Gly Asn Gly His Gly Thr His Val Ala Gly Thr Val
145                 150                 155                 160
Ala Ala Leu Gly Tyr Thr Thr Gly Val Leu Gly Val Ala Pro Ser Val
                165                 170                 175
Ser Leu Tyr Ala Val Lys Val Leu Asn Ser Ser Gly Ser Gly Ser Tyr
            180                 185                 190
Ser Gly Ile Val Ser Gly Ile Glu Trp Ala Thr Thr Asn Gly Met Asp
        195                 200                 205
Val Ile Asn Met Ser Leu Gly Gly Ala Ser Gly Ser Thr Ala Met Lys
    210                 215                 220
Gln Ala Val Asp Asn Ala Tyr Ala Lys Gly Val Val Val Val Ala Ala
225                 230                 235                 240
Ala Gly Asn Ser Gly Ser Ser Gly Ser Thr Asn Thr Ile Gly Tyr Pro
                245                 250                 255
Ala Lys Tyr Asp Ser Val Ile Ala Val Gly Ala Val Asp Ser Asn Ser
            260                 265                 270
Asn Arg Ala Ser Phe Ser Ser Val Gly Ala Glu Leu Glu Val Met Ala
        275                 280                 285
Pro Gly Ala Gly Val Tyr Ser Thr Tyr Pro Thr Asn Thr Tyr Ala Thr
    290                 295                 300
Phe Asn Gly Thr Ser Met Ala Ser Pro His Val Ala Gly Ala Ala Ala
305                 310                 315                 320
Leu Ile Leu Ser Lys His Pro Asn Leu Ser Ala Ser Gln Val Arg Asn
                325                 330                 335
Arg Leu Ser Ser Thr Ala Thr Tyr Leu Gly Ser Ser Phe Tyr Tyr Gly
            340                 345                 350
Lys Gly Leu Ile Asn Val Glu Ala Ala Ala Gln His His His His
        355                 360                 365
His
370                 375                 380

His
385

<210> SEQ ID NO 18
<211> LENGTH: 379
<212> TYPE: PRT
<213> ORGANISM: Artificial Sequence
<220> FEATURE:
<223> OTHER INFORMATION: variant subtilisin Carlsberg sequence

<400> SEQUENCE: 18

```
Met Met Arg Lys Lys Ser Phe Trp Leu Gly Met Leu Thr Ala Phe Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp
65                  70                  75                  80

Lys Glu Ala Leu Lys Glu Val Asn Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Phe Lys Gly
        115                 120                 125

Ala Asn Val Lys Val Ala Val Leu Asp Thr Gly Ile Gln Ala Ser His
    130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175

Ala Ala Leu Gly Tyr Thr Thr Gly Val Leu Gly Val Ala Pro Ser Val
            180                 185                 190

Ser Leu Tyr Ala Val Lys Val Leu Asn Ser Ser Gly Ser Gly Ser Tyr
        195                 200                 205

Ser Gly Ile Val Ser Gly Ile Glu Trp Ala Thr Thr Asn Gly Met Asp
    210                 215                 220

Val Ile Asn Met Ser Leu Gly Gly Ala Ser Gly Ser Thr Ala Met Lys
225                 230                 235                 240

Gln Ala Val Asp Asn Ala Tyr Ala Lys Gly Val Val Val Ala Ala
                245                 250                 255

Ala Gly Asn Ser Gly Ser Ser Gly Ser Thr Asn Thr Ile Gly Tyr Pro
            260                 265                 270

Ala Lys Tyr Asp Ser Val Ile Ala Val Gly Ala Val Asp Ser Asn Ser
        275                 280                 285

Asn Arg Ala Ser Phe Ser Ser Val Gly Ala Glu Leu Glu Val Met Ala
    290                 295                 300

Pro Gly Ala Gly Val Tyr Ser Thr Tyr Pro Thr Asn Thr Tyr Ala Thr
305                 310                 315                 320

Phe Asn Gly Thr Ser Met Ala Ser Pro His Val Ala Gly Ala Ala Ala
                325                 330                 335

Leu Ile Leu Ser Lys His Pro Asn Leu Ser Ala Ser Gln Val Arg Asn
            340                 345                 350

Arg Leu Ser Ser Thr Ala Thr Tyr Leu Gly Ser Ser Phe Tyr Tyr Gly
        355                 360                 365

Lys Gly Leu Ile Asn Val Glu Ala Ala Gln
    370                 375
```

<210> SEQ ID NO 19
<211> LENGTH: 24
<212> TYPE: DNA
<213> ORGANISM: Artificial Sequence -continued
<220> FEATURE:
<223> OTHER INFORMATION: Primer

<400> SEQUENCE: 19
tcagcccaag ctttctagag tcca                                          24

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
gaattccccg gatccgtcaa c                                             21

<210> SEQ ID NO 21
<211> LENGTH: 43
<212> TYPE: DNA
<213> ORGANISM: Artificial Sequence
<220> FEATURE:
<223> OTHER INFORMATION: Primer

<400> SEQUENCE: 21
atcaatctcc tatcctatat ggactctaga aagcttgggc tga                     43

<210> SEQ ID NO 22
<211> LENGTH: 41
<212> TYPE: DNA
<213> ORGANISM: Artificial Sequence
<220> FEATURE:
<223> OTHER INFORMATION: Primer

<400> SEQUENCE: 22
tgagatcaac agtttgggca gttgacggat ccggggaatt c                       41

<210> SEQ ID NO 23
<211> LENGTH: 356
<212> TYPE: PRT
<213> ORGANISM: Artificial Sequence
<220> FEATURE:
<223> OTHER INFORMATION: Subtilisin variant proprotein

<400> SEQUENCE: 23

Ala Gln Pro Ala Lys Asn Val Glu Lys Asp Tyr Ile Val Gly Phe Lys
1               5                   10                  15

Ser Gly Val Lys Thr Ala Ser Val Lys Lys Asp Ile Ile Lys Glu Ser
            20                  25                  30

Gly Gly Lys Val Asp Lys Gln Phe Arg Ile Ile Asn Ala Ala Lys Ala
        35                  40                  45

Lys Leu Asp Lys Glu Ala Leu Lys Glu Val Lys Asn Asp Pro Asp Val
    50                  55                  60

Ala Tyr Val Glu Glu Asp His Val Ala His Ala Leu Ala Gln Thr Val
65                  70                  75                  80

Pro Tyr Gly Ile Pro Leu Ile Lys Ala Asp Lys Val Gln Ala Gln Gly
                85                  90                  95

Phe Lys Gly Ala Asn Val Lys Val Ala Val Leu Asp Thr Gly Ile Gln
            100                 105                 110

Ala Ser His Pro Asp Leu Asn Val Val Gly Gly Ala Ser Phe Val Ala
        115                 120                 125

Gly Glu Ala Tyr Asn Thr Asp Gly Asn Gly His Gly Thr His Val Ala
    130                 135                 140

```
Gly Thr Val Ala Ala Leu Gly Asn Thr Thr Gly Val Leu Gly Val Ala
145                 150                 155                 160

Pro Ser Val Ser Leu Tyr Ala Val Lys Val Leu Asn Ser Ser Gly Ser
            165                 170                 175

Gly Ser Tyr Ser Gly Ile Val Ser Gly Ile Glu Trp Ala Thr Thr Asn
            180                 185                 190

Gly Met Asp Val Ile Asn Met Ser Leu Gly Gly Ala Ser Gly Ser Thr
            195                 200                 205

Ala Met Lys Gln Ala Val Asp Asn Ala Tyr Ala Lys Gly Val Val Val
        210                 215                 220

Val Ala Ala Ala Gly Asn Ser Gly Ser Ser Gly Asn Thr Asn Thr Ile
225                 230                 235                 240

Gly Tyr Pro Ala Lys Tyr Asp Ser Val Ile Ala Val Gly Ala Val Asp
                245                 250                 255

Ser Asn Ser Asn Arg Ala Ser Phe Ser Ser Val Gly Ala Glu Leu Glu
            260                 265                 270

Val Met Ala Pro Gly Ala Gly Val Tyr Ser Thr Tyr Pro Thr Asn Thr
            275                 280                 285

Tyr Ala Thr Leu Asn Gly Thr Ser Met Ala Ser Pro His Val Ala Gly
        290                 295                 300

Ala Ala Ala Leu Ile Met Ser Lys His Pro Asn Leu Ser Ala Ser Gln
305                 310                 315                 320

Val Arg Asn Arg Leu Ser Ser Thr Ala Thr Tyr Leu Gly Ser Ser Phe
                325                 330                 335

Tyr Tyr Gly Lys Gly Leu Ile Asn Val Glu Ala Ala Pro His His
            340                 345                 350

His His His His
        355

<210> SEQ ID NO 24
<211> LENGTH: 350
<212> TYPE: PRT
<213> ORGANISM: Artificial Sequence
<220> FEATURE:
<223> OTHER INFORMATION: Subtilisin variant proprotein

<400> SEQUENCE: 24

Ala Gln Pro Ala Lys Asn Val Glu Lys Asp Tyr Ile Val Gly Phe Lys
1               5                   10                  15

Ser Gly Val Lys Thr Ala Ser Val Lys Lys Asp Ile Ile Lys Glu Ser
            20                  25                  30

Gly Gly Lys Val Asp Lys Gln Phe Arg Ile Ile Asn Ala Ala Lys Ala
        35                  40                  45

Lys Leu Asp Lys Glu Ala Leu Lys Glu Val Lys Asn Asp Pro Asp Val
50                  55                  60

Ala Tyr Val Glu Glu Asp His Val Ala His Ala Leu Ala Gln Thr Val
65                  70                  75                  80

Pro Tyr Gly Ile Pro Leu Ile Lys Ala Asp Lys Val Gln Ala Gln Gly
                85                  90                  95

Phe Lys Gly Ala Asn Val Lys Val Ala Val Leu Asp Thr Gly Ile Gln
            100                 105                 110

Ala Ser His Pro Asp Leu Asn Val Val Gly Gly Ala Ser Phe Val Ala
        115                 120                 125

Gly Glu Ala Tyr Asn Thr Asp Gly Asn Gly His Gly Thr His Val Ala
130                 135                 140
```

```
Gly Thr Val Ala Ala Leu Gly Asn Thr Thr Gly Val Leu Gly Val Ala
145                 150                 155                 160

Pro Ser Val Ser Leu Tyr Ala Val Lys Val Leu Asn Ser Ser Gly Ser
                165                 170                 175

Gly Ser Tyr Ser Gly Ile Val Ser Gly Ile Glu Trp Ala Thr Thr Asn
            180                 185                 190

Gly Met Asp Val Ile Asn Met Ser Leu Gly Gly Ala Ser Gly Ser Thr
        195                 200                 205

Ala Met Lys Gln Ala Val Asp Asn Ala Tyr Ala Lys Gly Val Val Val
    210                 215                 220

Val Ala Ala Ala Gly Asn Ser Gly Ser Ser Gly Asn Thr Asn Thr Ile
225                 230                 235                 240

Gly Tyr Pro Ala Lys Tyr Asp Ser Val Ile Ala Val Gly Ala Val Asp
                245                 250                 255

Ser Asn Ser Asn Arg Ala Ser Phe Ser Ser Val Gly Ala Glu Leu Glu
            260                 265                 270

Val Met Ala Pro Gly Ala Gly Val Tyr Ser Thr Tyr Pro Thr Asn Thr
        275                 280                 285

Tyr Ala Thr Leu Asn Gly Thr Ser Met Ala Ser Pro His Val Ala Gly
    290                 295                 300

Ala Ala Ala Leu Ile Met Ser Lys His Pro Asn Leu Ser Ala Ser Gln
305                 310                 315                 320

Val Arg Asn Arg Leu Ser Ser Thr Ala Thr Tyr Leu Gly Ser Ser Phe
                325                 330                 335

Tyr Tyr Gly Lys Gly Leu Ile Asn Val Glu Ala Ala Pro
            340                 345                 350

<210> SEQ ID NO 25
<211> LENGTH: 275
<212> TYPE: PRT
<213> ORGANISM: Artificial Sequence
<220> FEATURE:
<223> OTHER INFORMATION: Mature subtilisin variant protein

<400> SEQUENCE: 25

Ala Gln Thr Val Pro Tyr Gly Ile Pro Leu Ile Lys Ala Asp Lys Val
1               5                   10                  15

Gln Ala Gln Gly Phe Lys Asn Val Lys Val Ala Val Leu Asp Thr Gly
            20                  25                  30

Ile Gln Ala Ser His Pro Asp Leu Asn Val Val Gly Gly Ala Ser Phe
        35                  40                  45

Val Ala Gly Glu Ala Tyr Asn Thr Asp Gly Asn Gly His Gly Thr His
    50                  55                  60

Val Ala Gly Thr Val Ala Leu Gly Asn Thr Thr Gly Val Leu Gly
65                  70                  75                  80

Val Ala Pro Ser Val Ser Leu Tyr Ala Val Lys Val Leu Asn Ser Ser
                85                  90                  95

Gly Ser Gly Ser Tyr Ser Gly Ile Val Ser Gly Ile Glu Trp Ala Thr
            100                 105                 110

Thr Asn Gly Met Asp Val Ile Asn Met Ser Leu Gly Gly Ala Ser Gly
        115                 120                 125

Ser Thr Ala Met Lys Gln Ala Val Asp Asn Ala Tyr Ala Lys Gly Val
    130                 135                 140

Val Val Val Ala Ala Gly Asn Ser Gly Ser Ser Gly Asn Thr Asn Thr
145                 150                 155                 160
```

```
Ile Gly Tyr Pro Ala Lys Tyr Asp Ser Val Ile Ala Val Gly Ala Val
                165                 170                 175

Asp Ser Asn Ser Asn Arg Ala Ser Phe Ser Ser Val Gly Ala Glu Leu
            180                 185                 190

Glu Val Met Ala Pro Gly Ala Gly Tyr Ser Thr Tyr Pro Thr Asn Thr
        195                 200                 205

Tyr Ala Thr Leu Asn Gly Thr Ser Met Ala Ser Pro His Val Ala Gly
    210                 215                 220

Ala Ala Ala Leu Ile Met Ser Lys His Pro Asn Leu Ser Ala Ser Gln
225                 230                 235                 240

Val Arg Asn Arg Leu Ser Ser Thr Ala Thr Tyr Leu Gly Ser Ser Phe
                245                 250                 255

Tyr Tyr Gly Lys Gly Leu Ile Asn Val Glu Ala Ala Pro His His
            260                 265                 270

His His His
        275

<210> SEQ ID NO 26
<211> LENGTH: 270
<212> TYPE: PRT
<213> ORGANISM: Artificial Sequence
<220> FEATURE:
<223> OTHER INFORMATION: Mature subtilisin variant protein

<400> SEQUENCE: 26

Ala Gln Thr Val Pro Tyr Gly Ile Pro Leu Ile Lys Ala Asp Lys Val
1               5                   10                  15

Gln Ala Gln Gly Phe Lys Asn Val Lys Val Ala Val Leu Asp Thr Gly
            20                  25                  30

Ile Gln Ala Ser His Pro Asp Leu Asn Val Val Gly Gly Ala Ser Phe
        35                  40                  45

Val Ala Gly Glu Ala Tyr Asn Thr Asp Gly Asn Gly His Gly Thr His
    50                  55                  60

Val Ala Gly Thr Val Ala Ala Leu Gly Asn Thr Thr Gly Val Leu Gly
65                  70                  75                  80

Val Ala Pro Ser Val Ser Leu Tyr Ala Val Lys Val Leu Asn Ser Ser
                85                  90                  95

Gly Ser Gly Ser Tyr Ser Gly Ile Val Ser Gly Ile Glu Trp Ala Thr
            100                 105                 110

Thr Asn Gly Met Asp Val Ile Asn Met Ser Leu Gly Gly Ala Ser Gly
        115                 120                 125

Ser Thr Ala Met Lys Gln Ala Val Asp Asn Ala Tyr Ala Lys Gly Val
    130                 135                 140

Val Val Val Ala Ala Gly Asn Ser Gly Ser Ser Gly Asn Thr Asn Thr
145                 150                 155                 160

Ile Gly Tyr Pro Ala Lys Tyr Asp Ser Val Ile Ala Val Gly Ala Val
                165                 170                 175

Asp Ser Asn Ser Asn Arg Ala Ser Phe Ser Ser Val Gly Ala Glu Leu
            180                 185                 190

Glu Val Met Ala Pro Gly Ala Gly Tyr Ser Thr Tyr Pro Thr Asn Thr
        195                 200                 205

Tyr Ala Thr Leu Asn Gly Thr Ser Met Ala Ser Pro His Val Ala Gly
    210                 215                 220

Ala Ala Ala Leu Ile Met Ser Lys His Pro Asn Leu Ser Ala Ser Gln
225                 230                 235                 240
```

Val Arg Asn Arg Leu Ser Ser Thr Ala Thr Tyr Leu Gly Ser Ser Phe
            245                 250                 255

Tyr Tyr Gly Lys Gly Leu Ile Asn Val Glu Ala Ala Pro
            260                 265                 270

<210> SEQ ID NO 27
<211> LENGTH: 350
<212> TYPE: PRT
<213> ORGANISM: Artificial Sequence
<220> FEATURE:
<223> OTHER INFORMATION: Truncated subtilisin Carlsberg proprotein

<400> SEQUENCE: 27

Ala Gln Pro Ala Lys Asn Val Glu Lys Asp Tyr Ile Val Gly Phe Lys
1               5                   10                  15

Ser Gly Val Lys Thr Ala Ser Val Lys Lys Asp Ile Ile Lys Glu Ser
            20                  25                  30

Gly Gly Lys Val Asp Lys Gln Phe Arg Ile Ile Asn Ala Ala Lys Ala
        35                  40                  45

Lys Leu Asp Lys Glu Ala Leu Lys Glu Val Lys Asn Asp Pro Asp Val
    50                  55                  60

Ala Tyr Val Glu Glu Asp His Val Ala His Ala Leu Ala Gln Thr Val
65                  70                  75                  80

Pro Tyr Gly Ile Pro Leu Ile Lys Ala Asp Lys Val Gln Ala Gln Gly
            85                  90                  95

Phe Lys Gly Ala Asn Val Lys Val Ala Val Leu Asp Thr Gly Ile Gln
            100                 105                 110

Ala Ser His Pro Asp Leu Asn Val Val Gly Gly Ala Ser Phe Val Ala
        115                 120                 125

Gly Glu Ala Tyr Asn Thr Asp Gly Asn Gly His Gly Thr His Val Ala
    130                 135                 140

Gly Thr Val Ala Ala Leu Asp Asn Thr Thr Gly Val Leu Gly Val Ala
145                 150                 155                 160

Pro Ser Val Ser Leu Tyr Ala Val Lys Val Leu Asn Ser Ser Gly Ser
            165                 170                 175

Gly Ser Tyr Ser Gly Ile Val Ser Gly Ile Glu Trp Ala Thr Thr Asn
            180                 185                 190

Gly Met Asp Val Ile Asn Met Ser Leu Gly Gly Ala Ser Gly Ser Thr
        195                 200                 205

Ala Met Lys Gln Ala Val Asp Asn Ala Tyr Ala Lys Gly Val Val Val
    210                 215                 220

Val Ala Ala Ala Gly Asn Ser Gly Ser Ser Gly Asn Thr Asn Thr Ile
225                 230                 235                 240

Gly Tyr Pro Ala Lys Tyr Asp Ser Val Ile Ala Val Gly Ala Val Asp
            245                 250                 255

Ser Asn Ser Asn Arg Ala Ser Phe Ser Ser Val Gly Ala Glu Leu Glu
            260                 265                 270

Val Met Ala Pro Gly Ala Gly Val Tyr Ser Thr Tyr Pro Thr Asn Thr
        275                 280                 285

Tyr Ala Thr Leu Asn Gly Thr Ser Met Ala Ser Pro His Val Ala Gly
    290                 295                 300

```
Ala Ala Ala Leu Ile Leu Ser Lys His Pro Asn Leu Ser Ala Ser Gln
305                 310                 315                 320

Val Arg Asn Arg Leu Ser Ser Thr Ala Thr Tyr Leu Gly Ser Ser Phe
            325                 330                 335

Tyr Tyr Gly Lys Gly Leu Ile Asn Val Glu Ala Ala Ala Gln
            340                 345                 350

<210> SEQ ID NO 28
<211> LENGTH: 274
<212> TYPE: PRT
<213> ORGANISM: Artificial Sequence
<220> FEATURE:
<223> OTHER INFORMATION: Subtilisin Carlsberg mature protein

<400> SEQUENCE: 28

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Lys
130                 135                 140

Gly Val Val Val Val Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Leu Asn Gly Thr Ser Met Ala Ser Pro
210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln
```